(12) United States Patent
Nishinaga et al.

(10) Patent No.: US 9,500,649 B2
(45) Date of Patent: Nov. 22, 2016

(54) ANALYTICAL TOOL AND METHOD FOR DETERMINING A CONDITION OF AN ORAL CAVITY

(75) Inventors: Eiji Nishinaga, Tokyo (JP); Akira Uchiyama, Tokyo (JP); Naho Suzuki, Tokyo (JP); Tetsu Fukasawa, Tokyo (JP); Riichi Maki, Tokyo (JP); Akio Okubo, Kyoto (JP); Isao Fukuta, Kyoto (JP)

(73) Assignee: ARKRAY, Inc., Kyoto (JP)

(*) Notice: Subject to any disclaimer, the term of this patent is extended or adjusted under 35 U.S.C. 154(b) by 119 days.

(21) Appl. No.: 13/976,643

(22) PCT Filed: Dec. 27, 2011

(86) PCT No.: PCT/JP2011/080180
§ 371 (c)(1),
(2), (4) Date: Aug. 23, 2013

(87) PCT Pub. No.: WO2012/090995
PCT Pub. Date: Jul. 5, 2012

(65) Prior Publication Data
US 2015/0038350 A1 Feb. 5, 2015

(30) Foreign Application Priority Data
Dec. 28, 2010 (JP) ................. 2010-292967

(51) Int. Cl.
*G01N 33/569* (2006.01)
*G01N 33/543* (2006.01)
*G01N 33/68* (2006.01)
*G01N 33/53* (2006.01)
*C12Q 1/68* (2006.01)

(52) U.S. Cl.
CPC ......... *G01N 33/56955* (2013.01); *C12Q 1/689* (2013.01); *G01N 33/5302* (2013.01); *G01N 33/54386* (2013.01); *G01N 33/6893* (2013.01); *C12Q 2600/118* (2013.01); *C12Q 2600/16* (2013.01); *G01N 2800/18* (2013.01); *G01N 2800/50* (2013.01)

(58) Field of Classification Search
None
See application file for complete search history.

(56) References Cited

U.S. PATENT DOCUMENTS

| | | | | |
|---|---|---|---|---|
| 3,907,503 A * | 9/1975 | Betts | ................ | G01N 35/00029 356/39 |
| 5,051,358 A * | 9/1991 | Witt | ................ | C12Q 1/44 435/19 |
| 5,989,840 A * | 11/1999 | D'Angelo | ................ | C12Q 1/04 422/420 |
| 2002/0061495 A1* | 5/2002 | Mault | ................ | A61B 5/0088 433/215 |
| 2002/0177171 A1 | 11/2002 | Stromberg | | |
| 2005/0019772 A1 | 1/2005 | Weizenegger | | |
| 2006/0140818 A1* | 6/2006 | Sakamoto | ................ | G01N 33/523 422/400 |
| 2008/0019871 A1* | 1/2008 | Sakamoto | ................ | B01L 3/545 422/68.1 |
| 2009/0047691 A1* | 2/2009 | Huwig | ................ | G01N 33/558 435/7.34 |
| 2009/0197285 A1 | 8/2009 | Hirschowitz et al. | | |

FOREIGN PATENT DOCUMENTS

| | | |
|---|---|---|
| EP | 0404210 A2 | 12/1990 |
| JP | 02-232561 A | 9/1990 |
| JP | 05-168497 A | 7/1993 |
| JP | 11-326339 A | 11/1999 |
| JP | 2002-181815 A | 6/2002 |
| JP | 2002-516997 A | 6/2002 |
| JP | 2005-241335 A | 9/2005 |
| JP | 2007-183281 A | 7/2007 |
| JP | 2009-516178 A | 4/2009 |
| JP | 3151124 U | 6/2009 |

OTHER PUBLICATIONS

Tao et al. Salivary antimicrobial peptide expression and dental caries experience in children. Antimicrobial Agents and Chemotherapy, vol. 49, No. 9, pp. 3883-3888, Sep. 2005.*
Tenovuo et al. Application of a dehydrated test strip, Hemastix (Registered Trademark), for the assessment of gingivitis. Journal of Clinical Periodontology, vol. 5, pp. 206-212, 1978.*
Henskens et al. Protein composition of whole and parotid saliva in healthy and periodontitis subjects. Journal of Periodontal Research, vol. 31, pp. 57-65, 1996.*
Wu et al. Determination of urea in saliva. Proceedings of the Society for Experimental Biology and Medicine, vol. 76, No. 1, pp. 130-132, 1651.*
Wright et al. An observed correlation between ammonia concentration and acid production in saliva. Journal of Dental Research, vol. 32, No. 2, pp. 232-238, 1953.*
Sopapornamorn et al. Relationship between total salivary protein content and volatile sulfur compound levels in malodor patients. Oral Surg Oral Med Oral Pathol Oral Radiol Endod, vol. 103, pp. 655-660, 2007.*

(Continued)

*Primary Examiner* — Jennifer Dunston
(74) *Attorney, Agent, or Firm* — Morgan, Lewis & Bockius LLP

(57) ABSTRACT

A method of determining the condition of the oral cavity in a subject is provided by using an analytical tool comprising the following (A), (B), and (C):

(A) a reagent for measuring one or more parameters that reflect the dental caries risk for a test sample obtained from the oral cavity, (B) a reagent for measuring one or more parameters that reflect the periodontal disease risk for the test sample obtained from the oral cavity, and (C) a reagent for measuring one or more parameters that reflect the degree of oral cleanliness for the test sample obtained from the oral cavity.

14 Claims, 4 Drawing Sheets

(56) References Cited

OTHER PUBLICATIONS

Maki et al., "A Rapid Test for Caries Activity by Resazurin Disc," Journal of Dental Health, 32: 121-122 (1982).
Jensen et al., "A New Method for the Estimation of Mutans Streptococci in Human Saliva," Journal of Dental Research, 68: 468-471 (1989).
International Search Report issued in corresponding International Patent Application No. PCT/JP2011/080180 dated Apr. 3, 2012.
International Preliminary Report on Patentability and Written Opinion issued in International Patent Application No. PCT/JP2011/080180 dated Jul. 18, 2013.
Office Action issued in corresponding European Patent Application No. 11852613.6 dated Jul. 17, 2015.
Extended European Search Report issued in corresponding European Patent Application No. 11852613.6 dated, Nov. 3, 2014.
Aps et al., "Flow cytometry as a new method to quantify the cellular content of human saliva and its relation to gingivitis," Clinica Chimica Acta 321: 35-41 (2002).
Amano et al.; "Monitoring ammonia to assess halitosis," Oral Surgery, Oral Medicine, Oral Pathology, Oral Radiology and Endodontics, 94: 692-696 (2002).
Milanovich et al., "Total protein concentration and total bacterial load as measures of residual interproximal plague in comparative clinical trials," Journal of Clinical Periodontology, 35: 23-30 (2007).
Lara-Carnlio et al., "Effect of orthodontic treatment on saliva, plague and the levels of Streptococcus mutans and Lactobacillus," Medicina Oral, Patologia Oral Y Cirugia Bucal, 15: e924-e029 (2010).
Deepa et al., "Saliva as a potential diagnostic tool," Indian Journal of Medical Sciences; 64: 293-306 (2010).
Office Action issued in corresponding European Patent Application No. 11852613.6 dated Apr. 15, 2016.

* cited by examiner (A)

(B)

ANALYTICAL TOOL AND METHOD FOR DETERMINING A CONDITION OF AN ORAL CAVITY

A computer readable text file, entitled "SequenceListing.txt," created on or about Jun. 26, 2013 with a file size of about 2 kb contains the sequence listing for this application and is hereby incorporated by reference in its entirety.

TECHNICAL FIELD

The present invention relates to a method of determining the condition of the oral cavity of a subject, and an analytical tool, an apparatus, and a program that can be used for the method.

BACKGROUND ART

It is crucially important for prevention or treatment of various oral diseases to know the condition of the oral cavity, that is, the risk for oral disease and the status of oral hygiene. Hence, development of methods for determining the risk for oral disease and the status of oral hygiene is strongly demanded. The risk for oral disease refers to, for example, the dental caries risk, that is how likely the oral cavity is to be affected by dental caries, the periodontal disease risk, that is, how likely the oral cavity is to be affected by periodontal diseases, and the like. Conventionally, diagnosis of the risk for oral disease and the status of oral hygiene has been carried out by a doctor or the like based on measurement results obtained by measuring individual component or property that reflects the risk for oral disease or the status of oral hygiene using saliva or gargle liquid collected from a subject as a sample.

For example, the mutans bacteria count in saliva, the acid buffering ability of saliva, or the like is known to reflect the dental caries risk. Either when the mutans bacteria count is high or when the acid buffering ability is low, the dental caries risk is considered to be high. Here, as methods for detecting mutans bacteria, a detection method using an antibody (Patent Document 1), a detection method using resazurin which is an oxidation-reduction indicator (Non-patent Document 1), and the like have been already known.

Further, for example, occult blood, leukocyte, alkaline phosphatase, or the like is known to reflect the periodontal disease risk. That is, when the periodontal disease is accompanied by destruction of gum tissues, the occult blood is detected in saliva and leukocytes gather to an area affected by the periodontal disease. Further, a large amount of alkaline phosphatase is produced by bacteria related to the periodontal disease. Here, as a method for detecting the occult blood, for example, a hemoglobin contact activation method is known (Patent Document 2). Also, as a method for detecting the leukocytes, a detection method utilizing esterase activity or protease activity of leukocytes is known (Patent Document 3).

Examples of examination systems for the disease of the oral cavity that have been in practical use will be described below.

As an examination system related to bacteria causing the periodontal disease, known is a system capable of evaluating the degree of infection and the type of infection for bacteria causing the periodontal disease, wherein blood is collected at home and mailed in a specialized container to measure the level of plasma antibodies against four types of the bacteria causing the periodontal disease. However, this system is only able to carry out the examination for the bacteria causing the periodontal disease and requires six business days for the result to become available.

Further as an examination system related to the periodontal disease, known is a system capable of determining incidence of the periodontal disease by detecting the occult blood in saliva. According to this system, the examination can be carried out in as short as 5 minutes but items other than the occult blood cannot be examined.

Further, as examination system related to the dental caries and periodontal disease, known is a system for detecting mutans bacteria and bacteria causing the periodontal disease by a PCR method using saliva collected in a dental clinic as a sample. According to this system, two items of the count of mutans bacteria and the count of the bacteria causing the periodontal disease can be simultaneously examined but six business days are required for the result to become available.

Further, as a system for detecting mutans bacteria, known is a system capable of detecting mutans bacteria by measuring a reaction of reducing resazurin by mutans bacteria. However, this system is able to carry out only the measurement of mutans bacteria, requires temperature adjustment to 37° C., and takes as long as 15 minutes.

Further, as the system for detecting mutans bacteria, besides the above, known is a system for determining the mutans bacteria count on the basis of the density of colonies that were formed by culturing mutans bacteria in saliva in a selection medium (Non-patent Document 2). However, this system is able to carry out only the measurement of mutans bacteria, requires temperature adjustment to 37° C., and takes as long as 48 hours.

PRIOR ART REFERENCES

Patent Documents

[Patent Document 1] Japanese Patent Application Laid-Open Publication No. 2005-241335
[Patent Document 2] Japanese Patent Application Laid-Open Publication No. 2-232561
[Patent Document 3] Japanese Patent Application Laid-Open Publication No. 5-168497

Non-Patent Documents

[Non-patent Document 1] Journal of Dental Health 1982; 32(4): p. 121-122
[Non-patent Document 2] Journal of Dental Research (J Dent Res) 1989; 68: p. 468-471

SUMMARY OF THE INVENTION

Problems to be Solved by the Invention

As described above, several methods and systems have been already known as the methods and systems for detecting individual component that reflects the condition of the oral cavity, i.e., the risk for oral disease and the status of oral hygiene.

However, there were rooms for improvement in that those existing systems required advanced examination techniques by a technical expert, doctor, or the like or advanced examination equipment for the specific PCR method or the like. In addition, data obtained by the above method or system only show information on individual component or property of the oral cavity, and do not provided information more than that. That is, in cases where the above method or system is utilized, only 1 to 2 items of components or properties are measured with respect to each disease such as "dental caries" or "periodontal disease". That is, the risk level for an arbitrary disease has not been determined based on measurement results obtained by measuring plural parameters, or the risk levels for plural diseases have not been determined based on measurement results obtained by measuring plural parameters that reflect the respective diseases. Because of that, a doctor or dental hygienist (hereinafter may referred to also as "doctor or the like") have conveyed the measurement result by the above method or system directly to a subject or have evaluated the measurement result by coupling with her or his knowledge based on her or his experience, thereby putting the measurement result to use for the treatment or prevention of the oral disease in the subject. Thus, the objectivity and accuracy of the diagnosis depend on skills of the doctor or the like, and hence, objective and comprehensive diagnosis of the risk for oral disease and the status of oral hygiene that does not require special skills has not been attained. Moreover, in cases where the existing system is utilized, time for measuring each item is so long that the diagnosis and subsequent care instructions cannot be given in a single visit.

An object of the present invention is to provide a means of determining the condition of the oral cavity, that is, the risk for oral disease and/or the status of oral hygiene, in the subject.

Means for Solving the Problems

The present inventors came up with the notion that, by measuring parameters that reflect the dental caries risk, parameters that reflect the periodontal disease risk, and parameters that reflect the degree of oral cleanliness, determining the levels of the dental caries risk, the periodontal disease risk, and the degree of oral cleanliness based on those measurement results, and providing the determined results to a doctor or the like, the doctor or the like was able to make an objective and comprehensive diagnosis of the risk for oral disease and the status of oral hygiene without the need for special skills. They further came up with the notion that use of an analytical tool that comprised respective reagents for measuring the above parameters allowed the measurement to be carried out in a short period of time in one examination, thereby completing the present invention.

Accordingly, the present invention can be illustrated as described below.

[1] An analytical tool comprising the following (A), (B), and (C):
(A) a reagent for measuring one or more parameters that reflect the dental caries risk for a test sample obtained from the oral cavity;
(B) a reagent for measuring one or more parameters that reflect the periodontal disease risk for the test sample obtained from the oral cavity; and
(C) a reagent for measuring one or more parameters that reflect the degree of oral cleanliness for the test sample obtained from the oral cavity.

[2] The analytical tool according to [1], wherein the analytical tool is a test piece comprising a support carrier and absorptive carriers that hold the respective reagents and are supported by the support carrier.

[3] The analytical tool according to [1] or [2], wherein the parameter(s) that reflect the dental caries risk includes at least mutans bacteria count.

[4] The analytical tool according to any one of [1] to [3], wherein:
the parameter(s) that reflect the dental caries risk are parameter(s) selected from the group consisting of mutans bacteria count, pH, and acid buffering ability;
the parameter(s) that reflect the periodontal disease risk are parameter(s) selected from the group consisting of calcium concentration, total protein concentration, occult blood amount, and leukocyte count; and
the parameter(s) that reflect the degree of oral cleanliness are parameter(s) selected from the group consisting of ammonia concentration and total protein concentration.

[5] The analytical tool according to any one of [1] to [4] comprising one or more features selected from the following (a), (b), and (c):
(a) the parameters that reflect the dental caries risk consist of two or more parameters;
(b) the parameters that reflect the periodontal disease risk consist of two or more parameters; and
(c) the parameters that reflect the degree of oral cleanliness consist of two or more parameters.

[6] A method of determining the condition of the oral cavity in a subject using the analytical tool according to any one of [1] to [5], the method comprising the following (A), (B), and (C):
(A) the step of measuring one or more parameters that reflect the dental caries risk for a test sample obtained from the oral cavity and determining the level of the dental caries risk using the measured parameter(s) as an index(es);
(B) the step of measuring one or more parameters that reflect the periodontal disease risk for the test sample obtained from the oral cavity and determining the level of the periodontal disease risk using the measured parameter(s) as an index(es); and
(C) the step of measuring one or more parameters that reflect the degree of oral cleanliness for the test sample obtained from the oral cavity and determining the level of the degree of oral cleanliness using the measured parameter(s) as an index(es).

[7] The method according to [6] further comprising the step of displaying the determined level.

[8] The method according to [6] or [7] further comprising the step of displaying a comment based on the determined level.

Effect of the Invention

By the present invention, the parameters that reflect the condition of the oral cavity, that is, the risk for oral disease and/or the status of oral hygiene, can be measured, and the condition of the oral cavity can be determined based on the measurement results. To be specific, the level(s) of the dental caries risk, the periodontal disease risk, and/or the degree of oral cleanliness can be determined, and the determination results can be provided to the doctor or the like and/or the subject. The doctor or the like is able to make an objective and comprehensive diagnosis of the risk for oral disease and/or the status of oral hygiene in the subject based on the determination results without the need for special skills, and is able to offer objective explanation to the subject about the condition of the oral cavity of the subject. In addition, the subject is able to objectively understand the condition of his/her oral cavity based on the determination results. Therefore, the present invention brings about a significant effect on support for the diagnosis and treatment by the doctor. In addition, the subject becomes conscious of prevention and health.

Furthermore, the use of the analytical tool or analytical apparatus of the present invention, in particular, allows the measurement of plural components or properties that reflect the condition of the oral cavity to be carried out in a short period of time in a single examination, and the level(s) of the dental caries risk, the periodontal disease risk, and/or the degree of oral cleanliness can be immediately determined. By providing the determination results to the doctor or the like and/or the subject, the diagnosis of the condition of the oral cavity and even subsequent care instructions can be given in a single visit, which has been traditionally impossible.

MODE FOR CARRYING OUT THE INVENTION

Figure 1:
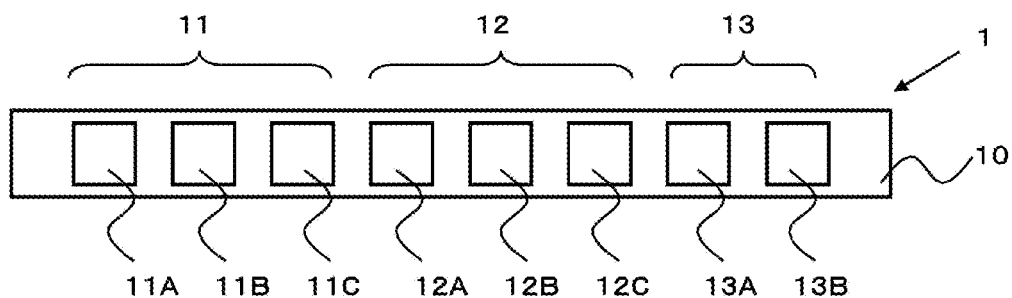
FIG. 1(A) is a plane view showing one embodiment of the analytical tool of the present invention.
FIG. 1(B) is a front view showing one embodiment of the analytical tool of the present invention.
Figure 1:
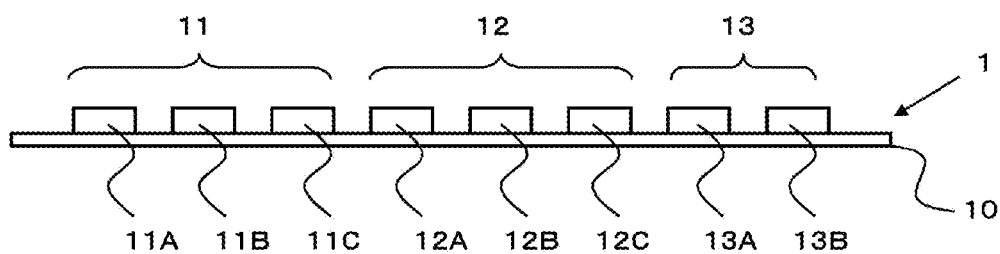

The present invention will now be described in detail below.

The condition of the oral cavity determined in the present invention refers to the risk for oral disease and/or the status of oral hygiene. The condition of the oral cavity determined in the present invention refers to, for example, the dental caries risk and the periodontal disease risk. Further, the status of oral hygiene determined in the present invention refers to, for example, the degree of oral cleanliness. Of these, the degree of oral cleanliness does not mean the risk for a specific disease but, in the present invention, the dental caries risk, the periodontal disease risk, and the degree of oral cleanliness may collectively be called as "risk". Further, similarly, in the present invention, the level of the dental caries risk, the level of the periodontal disease risk, and the level of the degree of oral cleanliness may collectively be called as "risk level". For convenience of explanation, it is referred to as "level" in this specification. The level is not necessary to be numerical values and may only be required to be classified into arbitrary stages.

The dental caries risk is a risk showing the likelihood of acquiring the dental caries and the likelihood of advancing the dental caries. In the present invention the dental caries risk includes not only a potential risk for developing the dental caries but also a condition of already having developed it. Examples of a parameter that reflects the dental caries risk include mutans bacteria count, pH, acid buffering ability, glucosyltransferase activity, sucrose concentration, glucose concentration, organic acid concentration, lactic acid concentration, reactivity with an antibody against mutans bacteria. In the present invention, it is preferred that one or two or more parameters selected from these parameters be measured. In the present invention, as the parameter that reflects the dental caries risk, it is preferred that one or two or more parameters selected from the group consisting of mutans bacteria count, pH, and acid buffering ability be measured, and it is more preferred that three parameters of mutans bacteria count, pH, and acid buffering ability be measured. In addition, it is preferred that at least mutans bacteria count be measured as the parameter that reflects the dental caries risk. With plural parameters being measured, the reliability upon determination of the level of the dental caries risk improves.

Mutans bacteria are so-called dental caries bacteria and are bacteria causing the dental caries. Specific examples of mutans bacteria include *Streptococcus mutans* and *Streptococcus sobrinus*. It is considered that the higher the mutans bacteria count is, the higher the dental caries risk is.

The pH of saliva is decreased due to acids produced by mutans bacteria. A large amount of the acids produced results in dissolution of enamel on the surface of teeth and progress of the dental caries. That is, it is considered that the lower the pH of saliva is, the higher the dental caries risk is.

The acid buffering ability indicates resistance against the acids produced by mutans bacteria. Thus, it is considered that the lower the acid buffering ability is, the higher the dental caries risk is.

The periodontal disease risk is a risk showing the likelihood of acquiring the periodontal disease and the likelihood of advancing the periodontal disease. In the present invention, the periodontal disease risk includes not only a potential risk for developing the periodontal disease but also a condition of already having developed it. Examples of a parameter that reflects the periodontal disease risk include calcium concentration, total protein concentration, occult blood amount, leukocyte count, alkaline phosphatase activity, nitrous acid concentration, lactate dehydrogenase activity, lipopolysaccharide concentration, reactivity with an antibody against periodontal disease-causing bacteria, γ-GTP concentration, albumin concentration, antioxidation degree, and α1-antitrypsin concentration. In the present invention, it is preferred that one or two or more parameters selected from these parameters be measured. In the present invention, as the parameter that reflects the periodontal disease risk, it is preferred that one or two or more parameters selected from the group consisting of calcium concentration, total protein concentration, occult blood amount, leukocyte count, alkaline phosphatase activity, and lactate dehydrogenase activity be measured. It is more preferred that one or two or more parameters selected from the group consisting of calcium concentration, total protein concentration, occult blood amount, and leukocyte count be measured. It is still more preferred that one or two or more parameters selected from the group consisting of total protein concentration, occult blood amount, and leukocyte count be measured. It is particularly preferred that three parameters of total protein concentration, occult blood amount, and leukocyte count be measured. With plural parameters being measured, the reliability upon determination of the level of the periodontal disease risk improves.

It is considered that the higher the total protein concentration in saliva is, the higher the periodontal disease risk is.

Further, when the periodontal disease is accompanied by destruction of gum tissues, the occult blood is detected in saliva. Thus, measurement of the level of the occult blood allows for measurement of the level of destruction of periodontal tissues. It is considered that the more the occult blood is, the higher the level of destruction of periodontal tissues is and the higher the periodontal disease risk is.

Further, because leukocytes gather to an area affected by of the periodontal disease, the measurement of the leukocytes allows for measurement of the level of inflammation of periodontal tissues. It is considered that the more the leukocyte count is, the higher the level of inflammation of periodontal tissues is and the higher the periodontal disease risk is.

The degree of oral cleanliness refers to, regardless of disease, a risk that reflects the status of oral hygiene. Examples of a parameter that reflects the degree of oral cleanliness include ammonia concentration, total protein concentration, total bacteria count, turbidity, viscosity, and secretion amount. In the present invention, it is preferred that one or two or more parameters selected from these parameters be measured. In the present invention, as the parameter that reflects the degree of oral cleanliness, it is preferred that at least one parameter selected from the group consisting of ammonia concentration and total protein concentration be measured, and it is more preferred that both parameters of ammonia concentration and total protein concentration be measured. With plural parameters being measured, the reliability upon determination of the level of the degree of oral cleanliness improves.

A high ammonia concentration indicates a condition in which bacteria are actively growing in the oral cavity. In addition, the higher the bacteria count is, the higher the total protein concentration is. Thus, it is considered that the higher the ammonia concentration is and the higher the total protein concentration is, the lower the degree of oral cleanliness is, that is, the higher the risk is.

In cases where the total protein concentration is at least selected as the parameter that reflects the periodontal disease risk and the total protein concentration is at least selected as the parameter that reflects the degree of oral cleanliness, it is sufficient that the total protein concentration is measured at least once. That is, the measurement result of the total protein concentration can be commonly utilized as the measurement result of the parameter that reflects the periodontal disease risk and the measurement result of the parameter that reflects the degree of oral cleanliness.

Further, in the present invention, by combining the parameter that corresponds to a certain specific risk with the parameter that corresponds to another risk to determine the risk level, the degree of accuracy in determining the risk level of said certain risk is expected to be improved. For example, by combining one or more parameters that reflect the dental caries risk with one or more parameters that reflect the periodontal disease risk and/or the degree of oral cleanliness to determine the dental caries risk level, the degree of accuracy in determining the dental caries risk level is expected to be improved. To be specific, for example, the dental caries risk level may be determined by combining the mutans bacteria count, pH, the acid buffering ability, the occult blood amount, the leukocyte count, the ammonia concentration, and the total protein concentration. The above description can be applied mutatis mutandis to the cases where the level of the periodontal disease risk or the level of the degree of oral cleanliness is determined.

Further, in the present invention, by combining the measurement result of the parameter described above with personal data of the subject, the degree of accuracy in determining the level of the dental caries risk, the level of the periodontal disease risk, and/or the level of the degree of the oral cleanliness is expected to be improved. Specific examples of the personal data of the subject include age, gender, and smoking habits.

In the present invention, the phrase "measuring the parameter" may only include the step of obtaining data for calculating an arbitrary parameter. It may or may not include the step of calculating such a parameter itself. That is, the value of each of the parameters can be quantified by measurement methods described later but the quantification of the value of the parameter itself is not an essential constituent feature of the present invention. For example, the phrase "measuring the mutans bacteria count" in the present invention may only obtain data to be used for calculating the mutans bacteria count, for example, reflectance data at an arbitrary wavelength showing a result of a color reaction that reflects the mutans bacteria count, and does not necessarily need to calculate the mutans bacteria count itself.

The measured parameter can be used for determination of the risk level. In the present invention, the term "determination" refers to determination of the risk level or the like by using the measured parameter as an index in comparison with a threshold level. Further, based on the determined risk level, the doctor or the like can make a diagnosis of the risk for oral disease and/or the status of oral hygiene in the subject. The term "diagnosis" refers to comprehensive assessment by the doctor or the like. Further, the term "care instructions" refers to, for example, instructions based on the diagnosis result, which care instructions are given by the doctor or the like.

(1) Analytical Tool of the Present Invention

The present invention provides an analytical tool that can be suitably used for measuring a parameter that reflects the condition of the oral cavity. The first aspect of the analytical tool of the present invention is an analytical tool comprising the following (A), (B), and (C):

(A) a reagent for measuring one or more parameters that reflect the dental caries risk for a test sample obtained from the oral cavity;

(B) a reagent for measuring one or more parameters that reflect the periodontal disease risk for the test sample obtained from the oral cavity; and (C) a reagent for measuring one or more parameters that reflect the degree of oral cleanliness for the test sample obtained from the oral cavity.

In reference to the drawings, the analytical tool of the present invention will be described below.

Figure 2:
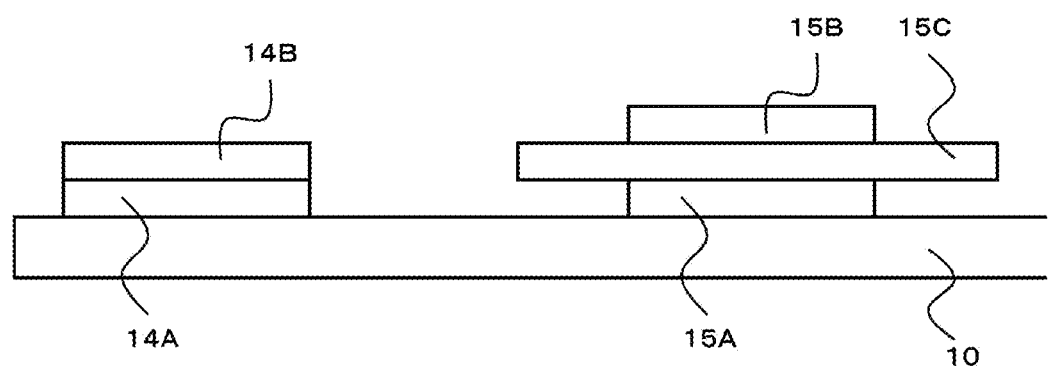
FIG. 2 is a front view showing the structure of the absorptive carrier portion in one embodiment of the analytical tool of the present invention.

One embodiment of the analytical tool of the present invention is a test piece (a piece for testing). The test piece, which is one embodiment of the analytical tool of the present invention, is also referred to as a test piece of the present invention. FIG. 1 illustrates, as an example, the test piece 1 that is one embodiment of the first aspect of the analytical tool of the present invention, the test piece 1 being configured so as to measure all of three of the dental caries risk, the periodontal disease risk, and the degree of oral cleanliness. FIG. 1(A) is a plane view of the test piece 1 and FIG. 1(B) is a front view of the test piece 1. FIG. 2 is a front view showing the structure of the absorptive carrier portion of the test piece in one embodiment of the analytical tool of the present invention.

The test piece 1 comprises the support carrier 10, and the measurement unit of the dental caries risk 11, the measurement unit of the periodontal disease risk 12, and the measurement unit of the degree of oral cleanliness 13, all of which are supported by the support carrier 10. The measurement units 11, 12, and 13 can have any positional relation thereamong.

The measurement unit of the dental caries risk 11 is a unit for measuring the parameter that reflects the dental caries risk in the subject and comprises the absorptive carriers 11A, 11B, and 11C. The absorptive carriers 11A, 11B, and 11C are absorptive carriers each of which holds a reagent for measuring the parameter that reflects the dental caries risk. The absorptive carrier 11A holds, for example, a reagent for measuring the mutans bacteria count for a test sample. The absorptive carrier 11B holds, for example, a reagent for measuring pH for a test sample. The absorptive carrier 11C holds, for example, a reagent for measuring the acid buffering ability for a test sample.

In the embodiment shown in FIG. 1, the measurement unit of the dental caries risk 11 comprises three absorptive carriers 11A, 11B, and 11C. Yet the number of the absorptive carriers equipped to the measurement unit of the dental caries risk 11 is increased or decreased according to the number of the parameters that reflect the dental caries risk to be measured, and usually at least one absorptive carrier is provided per one type of the parameter to be measured.

The measurement unit of the periodontal disease risk 12 is a unit for measuring the parameter that reflects the periodontal disease risk in the subject and comprises the absorptive carriers 12A, 12B, and 12C. The absorptive carriers 12A, 12B, and 12C are absorptive carriers each of which holds a reagent for measuring the parameter that reflects the periodontal disease risk. The absorptive carrier 12A holds, for example, a reagent for measuring the total protein concentration for a test sample. The absorptive carrier 12B holds, for example, a reagent for measuring the occult blood for a test sample. The absorptive carrier 12C holds, for example, a reagent for measuring the leukocyte count for a test sample.

In the embodiment shown in FIG. 1, the measurement unit of the periodontal disease risk 12 comprises three absorptive carriers 12A, 12B, and 12C. Yet the number of the absorptive carriers equipped to the measurement unit of the periodontal disease risk 12 is increased or decreased according to the number of the parameters that reflect the periodontal disease risk to be measured, and usually at least one absorptive carrier is provided per one type of the parameter to be measured.

The measurement unit of the degree of oral cleanliness 13 is a unit for measuring the parameter that reflects the degree of oral cleanliness in the subject and comprises the absorptive carriers 13A and 13B. The absorptive carriers 13A and 13B are absorptive carriers each of which holds a reagent for measuring the parameter that reflects the degree of oral cleanliness. The absorptive carrier 13A holds, for example, a reagent for measuring the ammonia concentration for a test sample. The absorptive carrier 13B holds, for example, a reagent for measuring the total protein concentration for a test sample.

In the embodiment shown in FIG. 1, the measurement unit of the degree of oral cleanliness 13 comprises two absorptive carriers 13A and 13B. Yet the number of the absorptive carriers equipped to the measurement unit of the degree of oral cleanliness 13 is increased or decreased according to the number of the parameters that reflect the degree of oral cleanliness to be measured, and usually at least one absorptive carrier is provided per one type of the parameter to be measured.

The above parameters described as the parameters that reflect the dental caries risk, the parameters that reflect the periodontal disease risk, and the parameters that reflect the degree of oral cleanliness are merely illustrative and are not limited to the above parameters. Details of each of the parameters will be described later.

Further, FIG. 1 describes an embodiment in which the absorptive carriers for measuring the respective parameters are placed in an orderly array while being sectioned into the measurement unit of the dental caries risk 11, the measurement unit of the periodontal disease risk 12, and the measurement unit of the degree of oral cleanliness 13, but the absorptive carriers for measuring the respective parameters can have any positional relation thereamong. That is, the absorptive carriers for measuring the respective parameters may not be placed in an orderly array while being sectioned into the measurement units for the respective risks. Further, the absorptive carriers for measuring the respective parameters may be linearly arranged or may be placed in any arrangement other than the linear arrangement. The positional relation among the absorptive carriers for measuring the respective parameters can be appropriately set, for example, according to whether the detection is carried out by the naked eye or by using a detection apparatus, and according to the type of the detection apparatus or the like. For example, various reflectance measurement devices can be suitably used as the detection apparatus, and in cases where PocketChem UA PU-4010 (manufactured by Arkray, Inc.) is used as the detection device, it is preferred that the absorptive carriers for measuring the respective parameters be linearly arranged. Further, the test piece of the present invention may comprise, in addition to the absorptive carrier that holds the reagent for measuring each of the parameters, any absorptive carrier, for example, a dummy absorptive carrier that is not used for the measurement.

In cases where the total protein concentration is at least selected as the parameter that reflects the periodontal disease risk and the total protein concentration is at least selected as the parameter that reflects the degree of oral cleanliness, it is sufficient that the analytical tool of the present invention comprises at least one absorptive carrier for measuring the total protein concentration. That is, the carrier for measuring the total protein concentration can be commonly used as the carrier for measuring the parameter that reflects the periodontal disease risk and the carrier for measuring the parameter that reflects the degree of oral cleanliness.

As the absorptive carrier, any carrier can be used as long as it is capable of holding the reagent for measuring each of the parameters and does not hamper the measurement. That is, for example, paper, cellulose, porous ceramics, chemical fibers, synthetic resin woven fabrics, and synthetic resin nonwoven fabrics can be used as the absorptive carrier. Filter paper or glass fiber filter paper is preferred. As the filter paper or glass fiber filter paper, for example, commercially-available one can be suitably used.

As the support carrier, films, sheets, or plate-shaped carriers can be suitably used. The support carrier is preferably made of plastic. As the plastic, for example, various plastics such as polyethylene, polypropylene, polyester, and polyvinyl chloride can be used. As the support carrier, a film made of polyethylene terephthalate (PET) is in particular preferred. Further, the support carrier may be a composite material. A composite material of polyester and polyethylene, a composite material obtained by laminating polyethylene and aluminium, or other various composite materials can be used. The thickness of the support carrier is preferably 10 to 500 µm and more preferably 50 to 300 µm.

The absorptive carrier that holds the reagent may concurrently serve as an absorptive carrier to which the test sample is dropped. Further, separately from the absorptive carrier that holds the reagent, the absorptive carrier to which the test sample is dropped may be equipped. FIG. 2 shows an example where the absorptive carrier 14A that holds the reagent and absorptive carrier 14B to which the test sample is dropped make up a layered structure as an example where the absorptive carrier to which the test sample is dropped is equipped separately from the absorptive carrier that holds the reagent. In cases where the absorptive carrier to which the test sample is dropped is equipped separately from the absorptive carrier that holds a reagent, the absorptive carrier that holds the reagent and absorptive carrier to which the test sample is dropped make contact in principle. Yet, for example in cases where the measurement requires to be carried out without a direct contact between the test sample and reagent, both of the absorptive carriers can be placed without contacting each other. Examples of the embodiment in which both are placed without contacting each other include an embodiment in which both of the absorptive carriers are placed with a gap therebetween and an embodiment in which another layer is put between both of the absorptive carriers, such as an embodiment in which a film made of PET with fine holes or the like is put between both carriers. FIG. 2 shows an example where the absorptive carrier 15A that holds the reagent and absorptive carrier 15B to which the test sample is dropped are placed without contacting each other by putting the spacer 15C between both carriers. Further, the test piece of the present invention may comprise an arbitrary member, for example, the film made of PET or the like, between the absorptive carrier that holds a reagent and support carrier.

A method for producing the test piece of the present invention is not particularly restricted. The test piece of the present invention can be produced by supporting each of the absorptive carriers that preliminarily holds the reagent for measuring for each of the parameters on the support carrier. A technique of holding the reagent for measuring each of the parameters to the absorptive carrier is not particularly restricted and, for example, the absorptive carrier may be immersed in a reagent solution, or the reagent solution may be dropped or applied to the absorptive carrier. Of the above, it is preferred to immerse the absorptive carrier in the reagent solution. The reagent solution refers to a solution containing the reagent for measuring an arbitrary parameter. The step of holding the reagent on the absorptive carrier may include plural times of carrying out the step of immersion, dropping, application, or the like. The absorptive carrier that holds each of the reagents can be dried to use in subsequent steps. The test piece of the present invention can be produced by cutting the absorptive carrier that holds each of the reagents as necessary and supporting the absorptive carrier on the support carrier. Further, the test piece of the present invention may be produced by holding the reagent for measuring each of the parameters on each of the absorptive carriers that is preliminarily supported on the support carrier. In this case, it is preferred that the reagent for measuring each of the parameters be held to the absorptive carrier by dropping or applying the reagent solution to the absorptive carrier, and then the absorptive carrier be dried. In the test piece of the present invention, a method for supporting the absorptive carrier on the support carrier is not particularly restricted and, for example, an adhesion technique that is usually used can be suitably used. For example, the adhesion may be carried out with an adhesive tape or with an adhesive agent.

As each of the absorptive carriers equipped to the test piece of the present invention, an absorptive carrier that is designed according to a measurement technique for each of the parameters can be used. Further, as each of the absorptive carriers equipped to the test piece of the present invention, a known test piece for quantitatively measuring the parameter that reflects the dental caries risk, the periodontal disease risk, or the degree of oral cleanliness, such as a dry test piece that is used in a general urine test or the like or a dry test piece that is used in a general blood biochemistry test or the like, can be diverted to be used with appropriate improvement as necessary.

Further, in one embodiment of the test piece of the present invention, each of the reagents for measurement may be held directly on the test piece, not on the absorptive carrier. Examples of the embodiment in which the reagent is held directly on the test piece include an embodiment in which the reagent is held directly on the support carrier. Such a test piece can be produced, for example, by dropping or applying the reagent directly on the support carrier. As for plural parameters to be measured, the embodiment in which the reagent for measurement is held on the absorptive carrier and the embodiment in which the reagent is held directly on the test piece may be employed in combination.

Another embodiment of the analytical tool of the present invention is a kit containing the analytical tool that comprises the reagent for measuring each of the parameters. Examples of the analytical tool that comprises the reagent for measuring each of the parameters include a test strip for measuring each of the parameters. That is, a kit containing test strips for measuring the respective parameters to be measured may be used as the analytical tool of the present invention. For example, a kit for measurement containing a test strip for measuring the parameter that reflects the dental caries risk, a test strip for measuring the parameter that reflects the periodontal disease risk, and a test strip for measuring the parameter that reflects the degree of oral cleanliness is included within the scope of the analytical tool of the present invention. The analytical tool contained in the kit for measurement may be, for example, an analytical tool that is configured so as to measure each of the parameters in any combination. For example, the analytical tool for measuring the parameter that reflects the dental caries risk may be an analytical tool for measuring two or more parameters that reflect the dental caries risk. Further, for example, the analytical tool for measuring the parameter that reflects the periodontal disease risk may be an analytical tool for measuring two or more parameters that reflect the periodontal disease risk. Further, for example, the analytical tool for measuring the parameter that reflects the degree of oral cleanliness may be an analytical tool for measuring two or more parameters that reflect the degree of oral cleanliness. Further, for example, the kit for measurement may contain an analytical tool for measuring one or more parameters that reflect the dental caries risk and one or more parameters that reflect the periodontal disease risk, may contain an analytical tool for measuring one or more parameters that reflect the dental caries risk and one or more parameters that reflect the degree of oral cleanliness, or may contain an analytical tool for measuring one or more parameters that reflect the degree of oral cleanliness and one or more parameters that reflect the periodontal disease risk.

Further, examples of the analytical tool that comprises the reagent for measuring each of the parameters include a reaction system for measuring an arbitrary parameter. That is, for example, if a reaction with reagent is carried out in a vessel such as a tube, a kit that contains the vessel for reaction such as the tube for reaction containing the reagent for measuring each of the parameters may be used as the analytical tool of the present invention. For example, a kit for measurement that contains a tube for reaction containing the reagent for measuring the parameter that reflects the dental caries risk, a tube for reaction containing the reagent for measuring the parameter that reflects the periodontal disease risk, and a tube for reaction containing the reagent for measuring the parameter that reflects the degree of oral cleanliness is included within the scope of the analytical tool of the present invention.

In the present invention, a method for measuring each of the parameters is not particularly restricted, and those skilled in the art can appropriately set. For example, a newly developed method may be used or a known method may be used. Methods for measuring the parameters that may be measured in the present invention will be illustrated below.

<Mutans Bacteria Count>

The mutans bacteria count can be measured by, for example, but not limited to, a method using a reduction reaction of resazurin or a method using an antibody against mutans bacteria. The mutans bacteria count is preferably measured by the method using the reduction reaction of resazurin. This method using the reduction reaction of resazurin is designated as "resazurin method". Resazurin is an oxidation-reduction indicator and usually exists as an oxidation-type blue pigment, resazurin (wavelength of maximum absorption 605 nm). Resazurin is reduced by NADH generated by the metabolism of Gram-positive bacteria including mutans bacteria to be converted to a red-purple pigment (wavelength of maximum absorption 573 nm), resorufin. That is, the reduction of resazurin takes place in accordance with the viable count of mutans bacteria. Further, in the case of employing the resazurin method, the measurement reagent preferably contains, in addition to resazurin, 1-methoxy-5-methylphenazinium methosulfate (methoxy PMS). The case of containing methoxy PMS shows a beneficial effect on carrying out the measurement in reaction conditions of a short period of time at room temperature, as compared with the case of not containing methoxy PMS. The concentration of the reagent can be appropriately set and the concentration of methoxy PMS in a reagent solution in which an absorptive carrier is immersed is preferably 0.1 to 1 mM and more preferably 0.1 to 0.5 mM.

As the absorptive carrier for the measurement of the mutans bacteria count by the resazurin method, for example, a test strip produced by the following procedure can be placed onto a support carrier and used.

(1) Immerse a filter paper in a reagent solution. This reagent solution contains 30 mM sucrose, 0.2% polyvinyl alcohol, 100 mM phosphate buffer solution (pH 6), 0.1 mM methoxy PMS, and 0.12 mM resazurin.
(2) Dry the filter paper at 50° C. for 15 minutes.
(3) Cut the filter paper into strips of 5 mm in width.
(4) Adhere the strip to a PET film.
(5) Cut the above into strips for 5 mm in width to obtain test strips. It goes without saying that an absorptive carrier for the measurement of any other parameter can be produced by altering the composition of the reagent solution in the above procedure to a reagent composition for the measurement of the other parameter.

Reaction time can be appropriately set and is preferably 1 to 10 minutes. In addition, detection conditions when the detection is carried out by a detection apparatus can be appropriately set. For example, when the test strip produced by the above procedure is used and PocketChem UA PU-4010 (manufactured by Arkray, Inc.) is used as the detection apparatus, the measurement can be carried out with a reaction time of 5 minutes, a measurement wavelength of 635 nm, and a reference wavelength of 760 nm. In this condition, the progress of the reduction reaction of resazurin is detected as a decrease in absorbance of 635 nm, that is, an increase in reflectance when irradiated with light of 635 nm. Based on the measurement results, the amount of consumed resazurin can be calculated. From the amount of consumed resazurin, the mutans bacteria count can be calculated. In the present invention, it may be considered that the shown reduction reaction of resazurin is all attribute to mutans bacteria.

<pH of Saliva>

The pH of saliva is preferably measured by, for example, but not limited to, a pH indicator. As the pH indicator, any known pH indicator can be used. It is preferred to use a pH indicator showing a color change in the range of pH 2 to 9. It is more preferred to use a pH indicator showing a color change in the range of pH 3 to 8. In addition, as the pH indicator, plural pH indicators may be mixed to be used as necessary. For example, a composite reagent of bromocresol green and bromoxylenol blue can be suitably used. The concentration of pH indicator can be appropriately set and, for example, the concentration of bromocresol green in a reagent solution in which an absorptive carrier is immersed is preferably 0.1 to 0.6 mM and more preferably 0.1 to 0.4 mM and the concentration of bromoxylenol blue in the reagent solution is preferably 0.6 to 2 mM and more preferably 0.8 to 1.8 mM.

As the absorptive carrier for the pH measurement by the pH indicator, for example, a test strip for pH measurement of AUTION Sticks (manufactured by Arkray, Inc.) can be used. This test strip contains 0.07 mg of bromocresol green and 0.72 mg of bromoxylenol blue per 100 strips.

Reaction time can be appropriately set and is preferably 30 seconds to 5 minutes. In addition, detection conditions when the detection is carried out by a detection apparatus can be appropriately set. For example, when the test strip for pH measurement of AUTION Sticks (manufactured by Arkray, Inc.) is used as the absorptive carrier for the pH measurement and PocketChem UA PU-4010 (manufactured by Arkray, Inc.) is used as the detection apparatus, the measurement can be carried out with a reaction time of 60 seconds, a measurement wavelength of 635 nm, and a reference wavelength of 760 nm. Based on the measurement results, the pH can be calculated.

<Acid Buffering Ability of Saliva>

The acid buffering ability of saliva is preferably measured by, for example, but not limited to, a pH indicator. The principle of measurement uses the phenomenon that, when a test sample is brought into contact with an absorptive carrier that preliminarily contains an acid buffer and pH indicator, an indicated pH by the indicator is closer to the intrinsic pH of saliva if the acid buffering ability is higher whereas it is closer to a range more acidic than the intrinsic pH of saliva if the acid buffering ability is lower. As the pH indicator, any known pH indicator can be used. It is preferred to use a pH indicator showing a color change in the range of pH 2 to 9. It is more preferred to use a pH indicator showing a color change in the range of pH 3 to 8. In addition, as the pH indicator, plural pH indicators may be mixed to be used as necessary. For example, a composite reagent of bromocresol green and bromoxylenol blue can be suitably used. As the acid buffer, for example, a nonvolatile organic acid can be preferably used. Examples of the nonvolatile organic acid include citric acid, malic acid, tartaric acid, malonic acid, oxalic acid, sulfosalicylic acid, sulfanilic acid, benzoic acid, and tricarballylic acid. Of these, tartaric acid is more preferred. In addition, an inorganic acid such as metaphosphoric acid can be used as the acid buffer. Moreover, the acid buffer may be, for example, a buffering agent such as a mixture of potassium hydrogen phthalate and potassium phosphate. The concentration of the reagent can be appropriately set and, for example, the concentration of bromocresol green in a reagent solution in which an absorptive carrier is immersed is preferably 0.1 to 0.6 mM and more preferably 0.1 to 0.4 mM; the concentration of bromoxylenol blue in the reagent solution is preferably 0.6 to 2 mM and more preferably 0.8 to 1.8 mM; and the concentration of tartaric acid in the reagent solution is preferably 0.1 to 10 mM and more preferably 1 to 6 mM.

As the absorptive carrier for the measurement of the acid buffering ability by the pH indicator, for example a test strip produced by the following procedure can be placed onto a support carrier and used.

(1) Immerse a filter paper in a reagent solution. This reagent solution contains 0.2 mM bromocresol green, 1.2 mM bromoxylenol blue, 0.05% polyoxyethylene sorbitan monolaurate, 0.5% hydroxypropyl cellulose, and 2 mM tartaric acid.

(2) Dry the filter paper at 50° C. for 15 minutes.

(3) Cut the filter paper into strips of 5 mm in width.

(4) Adhere the strip to a PET film.

(5) Cut the above into strips for 5 mm in width to obtain test strips. It goes without saying that an absorptive carrier for the measurement of any other parameter can be produced by altering the composition of the reagent solution in the above procedure to a reagent composition for the measurement of the other parameter.

Reaction time can be appropriately set and is preferably 30 seconds to 5 minutes. In addition, detection conditions when the detection is carried out by a detection apparatus can be appropriately set. For example, when the test strip for pH measurement of AUTION Sticks (manufactured by Arkray, Inc.) is reformed as described above and used as the absorptive carrier for the measurement of the acid buffering ability and PocketChem UA PU-4010 (manufactured by Arkray, Inc.) is used as the detection apparatus, the measurement can be carried out with a reaction time of 60 seconds, a measurement wavelength of 635 nm, and a reference wavelength of 760 nm. Based on the measurement results, the pH can be calculated and in turn the acid buffering ability can be calculated.

<Calcium Concentration>

The calcium concentration is preferably measured by, for example, but not limited to, the chelate method. The chelate method refers to a method for measuring calcium using the phenomenon that, when calcium binds to a chelate color developing agent, color change takes place. As the chelate method, O-CPC method is preferably used. The O-CPC method is a measurement method in which o-cresolphthalein complexone (O-CPC) is used as the chelate color developing agent. O-CPC reacts with calcium under alkali conditions to yield a crimson red chelate compound.

As the absorptive carrier for the calcium concentration measurement by the chelate method, for example, a test strip included in SPOTCHEM II calcium (manufactured by Arkray, Inc.), which is a kit for calcium concentration measurement, can be used. This test strip contains 2.6 mg of O-CPC per 100 strips.

Reaction time can be appropriately set and is preferably 1 minute to 5 minutes. In addition, detection conditions when the detection is carried out by a detection apparatus can be appropriately set. For example, when the test strip included in SPOTCHEM II calcium (manufactured by Arkray, Inc.) is used as the absorptive carrier for the calcium concentration measurement and PocketChem UA PU-4010 (manufactured by Arkray, Inc.) is used as the detection apparatus, the measurement can be carried out with a reaction time of 90 seconds, a measurement wavelength of 565 nm, and a reference wavelength of 760 nm. Based on the measurement result, the amount of the chelate compound can be calculated. From the amount of the chelate compound, the calcium concentration can be calculated.

<Occult Blood>

The occult blood is preferably measured by, for example, but not limited to, the hemoglobin contact activation method. The hemoglobin contact activation method refers to a method using the phenomenon that hemoglobin, myoglobin, or a degradation product thereof, all of which are blood components, have an ability to catalyze oxygen transfer from an oxygen donor such as peroxide to an oxygen receptor (peroxidase-like activity). By employing an indicator that changes color thereof upon oxidation as the oxygen receptor and measuring a color reaction thereof, the occult blood is able to be detected through the detection of the hemoglobin or the like.

The indicator is not particularly restricted as long as the color reaction is induced by hemoglobin, myoglobin, or the degradation product thereof, all of which are blood components, and, for example, anilines, phenols, o-toluidine, p-toluidine, o-phenylene diamine, N,N'-dimethyl-p-phenylene diamine, N,N'-diethyl-p-phenylene diamine, p-anisidin, dianisidine, o-tolidine, o-cresol, m-cresol, p-cresol, α-naphthol, β-naphthol, catechol, guaiacol, pyrogallol, or the like can be used. As phenols, for example, 3,3',5,5'-tetramethylbenzidine (TMBZ) can be suitably used.

Further, as the oxygen donor, a peroxide is preferred. As the peroxide, for example, cumene hydroperoxide, diisopropylbenzene peroxide, paramenthane hydroperoxide, 2,5-dimethylhexane-2,5-dihydroperoxide, or the like is preferably used. As the oxygen donor, for example, cumene hydroperoxide can be suitably used.

As an absorptive carrier for the occult blood measurement by the hemoglobin contact activation method, for example, a test strip for occult blood measurement of AUTION Sticks (manufactured by Arkray, Inc.) can be used. This test strip contains 30.0 mg of cumene hydroperoxide and 15.0 mg of TMBZ per 100 strips.

Reaction time can be appropriately set and is preferably 30 seconds to 5 minutes. In addition, detection conditions when the detection is carried out by a detection apparatus can be appropriately set. For example, when the test strip for occult blood measurement of AUTION Sticks (manufactured by Arkray, Inc.) is used as the absorptive carrier for the occult blood measurement and PocketChem UA PU-4010 (manufactured by Arkray, Inc.) is used as the detection apparatus, the measurement can be carried out with a reaction time of 60 seconds and a measurement wavelength of 635 nm. Based on measurement results, the hemoglobin concentration can be calculated. From the hemoglobin concentration the occult blood amount can be calculated.

<The Leukocyte Count>

The leukocyte count is preferably measured by, for example, but not limited to, the leukocyte esterase method. When tissues develop inflammation, leukocytes increase, which is accompanied with increased production of esterase by the leukocytes. Hence, the leukocyte count can be calculated by measuring the esterase activity. The leukocyte esterase method is a technique of measuring the leukocyte count by directly developing a color of an alcohol (phenol) component that is generated by hydrolyzing an ester compound used as a substrate by the esterase produced by the leukocytes (leukocyte esterase), or by developing a color by coupling with a diazonium salt.

As the ester compound used as the substrate, in the case of the direct color development, sulfonphthalein esters, azo dye esters, or the like can be used. In the case of the color development by coupling with other indicators, phenoxyamino acid esters, indoxyl esters, phenylphenoxyl esters, or the like can be used. As the indoxyl esters, for example, 3-(N-toluenesulfonyl-L-alanyloxy)indole (TAI) can be suitably used. As the indicator in the case of the color development by coupling, a diazonium salt can be used and, for example, 2-methoxy-4-(N-morpholino)benzenediazonium salt can be suitably used. In cases where 3-(N-toluenesulfonyl-L-alanyloxy)indole is used as the ester compound, indoxyl generated by the reaction can be coupled with, for example, 2-methoxy-4-(N-morpholino)benzenediazonium salt (MMB), thereby developing the color.

As an absorptive carrier for the leukocyte measurement by the leukocyte esterase method, for example, a test strip for leukocyte measurement of AUTION Sticks (manufactured by Arkray, Inc.) can be used. This test strip contains 0.49 mg of TAI and 0.17 mg of MMB per 100 strips.

Reaction time can be appropriately set and is preferably 30 seconds to 5 minutes. In addition, detection conditions when the detection is carried out by a detection apparatus can be appropriately set. For example, when the test strip for leukocyte measurement of AUTION Sticks (manufactured by Arkray, Inc.) is used as the absorptive carrier for the leukocyte measurement and PocketChem UA PU-4010 (manufactured by Arkray, Inc.) is used as the detection apparatus, the measurement can be carried out with a reaction time of 60 seconds, a measurement wavelength of 565 nm, and a reference wavelength of 760 nm. Based on the measurement result, the esterase activity can be calculated. From the esterase activity, the leukocyte count can be calculated.

<Protein Concentration>

The total protein concentration is preferably measured by, for example, but not limited to, the protein error method. The protein error method refers to a method for measuring a protein using the phenomenon that a pH indicator shows a higher pH than the true pH of a solution in proportion to the concentration of the protein.

Examples of the pH indicator that can be utilized in the protein error method include tetrabromophenol blue (TBPB), tetrabromophenolphthalein, 5',5''-dinitro-3',3''-di-iodo-3,4,5,6-tetrabromophenol sulfophthalein (DIDNTB), Coomassie brilliant blue, Fast Green FCF, and Light Green SF (for example, see U.S. Pat. No. 4,013,416 or the like). Tetrabromophenol blue is suitably used. Further, in cases where the indicator is insoluble to water, a reagent solution can be prepared using an organic solvent such as acetone, ethanol, or methyl cellosolve. Further, because the color development also takes place by change in pH, a pH buffering agent is preferably present together. Further, because the reaction is carried out preferably under acidic conditions, an acid buffering agent is preferably used as the pH buffering agent. As the acid buffering agent, a nonvolatile organic acid can preferably be used. Examples of the nonvolatile organic acid include citric acid, malic acid, tartaric acid, malonic acid, oxalic acid, sulfosalicylic acid, sulfanilic acid, benzoic acid, and tricarballylic acid. In addition, an inorganic acid such as metaphosphoric acid can be used as the acid buffering agent. Moreover, the acid buffer may be, for example, a buffering agent such as a mixture of potassium hydrogen phthalate and potassium phosphate. The concentration of the acid buffering agent is preferably a concentration enough to prevent the color change of a protein error indicator upon a contact with a sample in which a significant amount of proteins is not present. For example, the buffering agent is preferably contained in a reagent solution for immersing, dropping, or applying at 50 to 1500 mM and more preferably at 1000 to 1200 mM.

As the absorptive carrier for the protein measurement by the protein error method, for example, a test strip for protein measurement of AUTION Sticks (manufactured by Arkray, Inc.) can be used. This test strip contains 0.35 mg of TBPB per 100 strips.

Reaction time can be appropriately set and is preferably 30 seconds to 5 minutes. In addition, detection conditions when the detection is carried out by a detection apparatus can be appropriately set. For example, when the test strip for protein measurement of AUTION Sticks (manufactured by Arkray, Inc.) is used as the absorptive carrier for the protein measurement and PocketChem UA PU-4010 (manufactured by Arkray, Inc.) is used as the detection apparatus, the measurement can be carried out with a reaction time of 60 seconds, a measurement wavelength of 635 nm, and a reference wavelength of 760 nm. Based on the measurement results, the total protein concentration can be calculated.

<Ammonia>

The quantification of ammonia is preferably carried out by, for example, but not limited to, the microdiffusion method (Conway method). The microdiffusion method refers to a technique used for quantifying ammonia nitrogen and a technique in which a component volatilized from a sample is trapped in a solution for absorption or the like to quantify by a technique such as colorimetry. In cases where the ammonia concentration is measured by the microdiffusion method, an absorptive carrier (sample layer) to which a test sample is dropped is equipped, separately from an absorptive carrier (reagent layer) that holds a reagent, in an ammonia quantification portion in the test piece of the present invention, and both of the absorptive carriers are placed so as not to contact each other. Both of the absorptive carriers are placed so as not to contact each other by, for example, putting a film made of PET having fine holes between both of the absorptive carriers. Further, the sample layer holds an alkali buffering agent, for example, boric acid buffering agent. When the test sample is dropped to the sample layer of the test piece, the alkali buffering agent in the sample layer becomes dissolved and the sample is alkalified. Ammonium ions in the sample become ammonia molecules under alkali conditions, vaporize as ammonia gas, and transfer to the reagent layer by, for example, passing through the holes of a spacer. The indicator in the reagent layer reacts with the ammonia gas, thereby developing color.

As a pH indicator, any known pH indicator can be used. As the pH indicator, for example, bromcresol green, bromcresol purple, chlorophenol red, or the like is used and bromcresol green is suitably used. In addition, as the pH indicator, plural pH indicators may be mixed to be used as necessary.

As the absorptive carrier for the ammonia measurement by the microdiffusion method, for example, a test strip included in Amicheck (manufactured by Arkray, Inc.), which is a kit for ammonia measurement, can be used. This test strip contains, per 100 strips, 42.6 mg of boric acid and 18.7 mg of sodium hydroxide in the sample layer, and 4.0 mg of bromcresol green in the reagent layer.

Reaction time can be appropriately set and is preferably 10 seconds to 5 minutes. In addition, detection conditions when the detection is carried out by a detection apparatus can be appropriately set. In cases where, for example, the test strip included in Amicheck (manufactured by Arkray, Inc.) is used as the absorptive carrier for the ammonia measurement and PocketChem UA PU-4010 (manufactured by Arkray, Inc.) is used as the detection apparatus, the sample layer and spacer can be detached from the reagent layer 20 seconds after the test sample is dropped to the sample layer, and the reagent layer can be measured with a measurement wavelength of 635 nm after 60 seconds. Based on the measurement result, the ammonia concentration can be calculated.

<Lactate Dehydrogenase Activity>

The lactate dehydrogenase activity is measured by, for example, but not limited to, the formazan method. The formazan method refers to a technique of reducing a tetrazolium salt to formazan, which is a coloring material, via diaphorase by NADH that is produced by the oxidation of lactic acid by lactate dehydrogenase using NAD as a coenzyme. As the tetrazolium salt, for example, tetrazolium violet can be suitably used.

<Alkaline Phosphatase Activity>

The alkaline phosphatase activity is measured by, for example, but not limited to, the p-nitrophenyl phosphoric acid method. The p-nitrophenyl phosphoric acid method refers to a technique of quantifying a coloring material, p-nitrophenol, which is produced by the hydrolyzation of a substrate, p-nitrophenyl phosphoric acid, by alkaline phosphatase.

Each of the above measurement methods can be suitably utilized in an absorptive carrier placed on the test piece of the present invention. In addition, not being limited to the case where the test piece that comprises the absorptive carrier is used, each of the above measurement methods can also be used, for example, in the case where a test piece that does not comprise the absorptive carrier is used and in the case where a reaction with a sample is carried out in a vessel such as a tube, by appropriately setting reagent concentration, reaction time, and the like. Therefore, the analytical tool of the present invention is suitably used for measuring each of the parameters that reflect the dental caries risk, the periodontal disease risk, and the degree of oral cleanliness in a short period of time and in a single examination. Further, use of the analytical tool of the present invention, an objective, reproducible, and reliable measurement can be carried out without depending on examination techniques of a laboratory technician, doctor, or the like.

The analytical tool of the present invention is configured so as to measure the above-mentioned parameters that reflect the dental caries risk, the periodontal disease risk, and the degree of oral cleanliness. That is, it is preferred, for example, that the analytical tool of the present invention be configured so as to measure one or more parameters selected from the group consisting of mutans bacteria count, pH, and acid buffering ability as the parameters that reflect the dental caries risk; to measure one or more parameters selected from the group consisting of calcium concentration, total protein concentration, occult blood amount, and leukocyte count as the parameters that reflect the periodontal disease risk; and to measure one or more parameters selected from the group consisting of ammonia concentration and total protein concentration as the parameters that reflect the degree of oral cleanliness. Further, it is also preferred that the analytical tool of the present invention be configured so as to measure mutans bacteria count, pH, and acid buffering ability as the parameters that reflect the dental caries risk; to measure calcium concentration, total protein concentration, occult blood amount, and leukocyte count as parameters that reflect the periodontal disease risk; and to measure ammonia concentration and total protein concentration as the parameters that reflect the degree of oral cleanliness. Furthermore, it is particularly preferred that the analytical tool of the present invention be configured so as to measure all of the 7 parameters consisting of mutans bacteria count, pH, acid buffering ability, occult blood amount, leukocyte count, ammonia concentration, and total protein concentration.

Further, the second aspect of the analytical tool of the present invention is an analytical tool that comprises reagents for measuring two or more parameters that reflect the dental caries risk for a test sample obtained from the oral cavity.

Further, the third aspect of the analytical tool of the present invention is, for example, an analytical tool that comprises reagents for measuring two or more parameters that reflect the periodontal disease risk for a test sample obtained from the oral cavity.

Further, the fourth aspect of the analytical tool of the present invention is, for example, an analytical tool that comprises reagents for measuring two or more parameters that reflect the degree of oral cleanliness for a test sample obtained from the oral cavity.

The description presented above in regard to the first aspect of the analytical tool of the present invention can be applied mutatis mutandis to the second, third, and fourth aspects of the analytical tool of the present invention.

(2) Measurement Apparatus of the Present Invention

Figure 3:
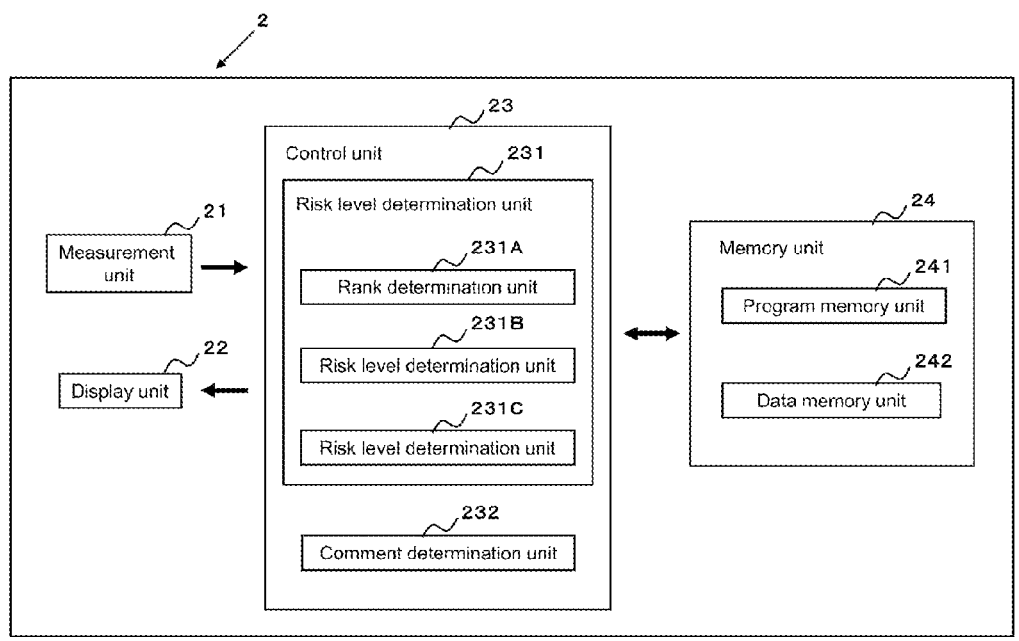
FIG. 3 is a block diagram showing functions in one embodiment of the apparatus of the present invention.

The first aspect of the measurement apparatus of the present invention is a measurement apparatus that comprises:

(A) a measurement unit for measuring, for a test sample obtained from the oral cavity, one or more parameters that reflect the dental caries risk, one or more parameters that reflect the periodontal disease risk, and one or more parameters that reflect the degree of oral cleanliness;

(B) a risk level determination unit for determining the levels of the dental caries risk, periodontal disease risk, and degree of oral cleanliness from the results measured by the measurement unit; and (C) a display unit for displaying the risk levels determined by the risk level determination unit as character, graphic, code, color, or a combination thereof. The measurement apparatus of the present invention is also a measurement apparatus that further comprises (D) a display unit for displaying comments based on the risk levels determined by the risk level determination unit. In reference to the drawings, the measurement apparatus of the present invention will be described below. FIG. 3 is a block diagram showing the functions of the measurement apparatus 2 which is one embodiment of the measurement apparatus of the present invention.

The measurement apparatus 2 comprises the measurement unit 21. The measurement unit 21 is a unit of obtaining measurement data of each of the parameters. For example, when the measurement of each of the parameters is carried out using the test piece of the present invention, the measurement unit 21 measures the progress of the color reaction in each of the absorptive carriers equipped to the test piece of the present invention.

The progress of the color reaction can be measured based on absorbance at a specific wavelength.

For example, when the measurement of each of the parameters is carried out using the test piece of the present invention, it is sufficient that reflectance data that correlates with the progress of the color reaction is obtained.

The reflectance data may be, for example, the value of the reflectance at the specific wavelength when a certain period of time passes after bringing a test sample into contact with the reagent for measuring each of the parameters. To be specific, the value of the reflectance can be obtained by irradiating light of the specific wavelength to a color developing portion, for example, an absorptive carrier portion to which the test sample is dropped, and measuring reflected light thereof. Further, the reflectance data may be, for example, the value obtained by dividing the value of the reflectance obtained as described the above from 100%. It can be said that the higher the absorbance at the specific wavelength is, the lower the value of the reflectance at such a specific wavelength is; and the lower the absorbance at the specific wavelength is, the higher the value of the reflectance at such a specific wavelength is. The certain period of time may be, for example, the reaction time in the method of measuring each of the parameters described above. The certain period of time may be appropriately set according to the type of the parameter to be measured or the measurement method.

Further, the reflectance data may be, for example, the value of change in the reflectance at a specific wavelength during the passage of a certain period of time. To be specific, the value of change in the reflectance can be obtained by irradiating light of the specific wavelength to a color developing portion, for example, an absorptive carrier portion to which the test sample is dropped, and measuring the increase or decrease of reflected light thereof. The increase in absorbance at the specific wavelength can be measured as a decrease in the reflectance at such a specific wavelength. The decrease in absorbance at the specific wavelength can be measured as an increase in the reflectance at such a specific wavelength. The certain period of time may be a period of time from immediately after dropping the test sample until when an arbitrary period of time passes, or may be a period of time from a certain time point after dropping the test sample until when an arbitrary period of time further passes. The length of the certain period of time and the certain time point after dropping the test sample may be appropriately set according to the type of the parameter to be measured or the measurement method. The value of change in the reflectance can be calculated as the difference between the measurement values obtained by measuring the reflectance at least twice. Further, the value of change in the reflectance during the passage of a certain period of time may be calculated as the rate of change of the reflectance based on the reflectance that is measured several times. In cases where the reflectance immediately after dropping the test sample or at the certain point of time after dropping the test sample is not required to be measured, such as in cases where the reflectance immediately after dropping the test sample or at the certain point of time after dropping the test sample is assumed to be constant, the number of times of measuring the reflectance may be reduced.

Whether either of the above values is employed as the reflectance data may be appropriately set according to the type of the parameter to be measured or the measurement method. For example, in cases where the mutans bacteria count is measured by the resazurin method, it is preferred to measure the value in change of the reflectance. To be specific, for example, in cases where the mutans bacteria count is measured by the resazurin method, if the reaction time is 5 minutes, the reflectance change during 4 minutes from the first minute to the fifth minute after the starting of the reaction may be measured. In addition, the use of either of the above values may be switched according to cases. For example, in cases where, at the specific wavelength, a parameter that exhibits lower reflectance as being deteriorated is measured, the reflectance may be used, and in contrast, in cases where a parameter that exhibits higher reflectance as being deteriorated is measured, a value obtained by dividing the value of the reflectance from 100% may be used. For example, in cases where pH is measured using a measurement reagent containing bromocresol green and bromoxylenol blue, the more the pH deteriorates, that is, the more acidic the pH becomes, the higher the reflectance at a measurement wavelength of 635 nm becomes. The wavelength of a source of light used for obtaining the reflectance data can be appropriately set based on the method for measuring each of the parameters or the detection apparatus used. Further, the wavelength for measurement and a reference wavelength for the purpose of removing effects of background may be set and used individually. Further, each of the parameters may be sequentially measured, or plural parameters may be simultaneously measured by an apparatus comprising plural photometrical units.

The measurement apparatus 2 comprises the controlling unit 23. The controlling unit 23 comprises CPU and RAM. By CPU interpreting and executing a program loaded into RAM, the controlling unit 23 functions as the risk level determination unit 231 comprising the rank determination unit 231A and two risk level determination units 231B and 231C and the comment determination unit 232, which are described later. The above program is stored in the program memory unit 241 of the memory unit 24 described later.

The risk level determination unit 231 is comprised in the controlling unit 23 and comprises the rank determination unit 231A and two risk level determination units 231B and 231C.

The rank determination unit 231A determines the rank of each of the parameters for a test sample based on a table in which correlation between the rank of the parameter that reflects the dental caries risk, the periodontal disease risk, or the degree of oral cleanliness and the reflectance data is defined, the table being stored in the memory unit 24 described later. For example, based on a table in which correlation between the rank of the mutans bacteria count and the reflectance data is defined, the rank of the mutans bacteria count is determined for the test sample. The determined rank is composed of two stages or more, or preferably three to eight stages.

The risk level determination unit 231B determines to which risk level the determined rank of the parameter determined by the rank determination unit 231A corresponds to in the risk that the parameter reflects based on a table in which correlation between the rank of each of the parameters and the level of the risk that the parameter reflects is defined, the table being stored in the memory unit 24 described later. For example, based on a table showing correlation between the rank of the mutans bacteria count and the level of the dental caries risk, the determined rank of the mutans bacteria count determined by the rank determination unit 231A is determined to correspond to which risk level in the dental caries risk.

The risk level determination unit 231C calculates the level of the risk for each of the risks, based on the risk level of the parameter that reflects the risk determined by the risk level determination unit 231B in the risk. For example, based on the risk levels of mutans bacteria count, pH, and acid buffering ability in the dental caries risk, which risk levels are determined by the risk level determination unit 231B, the dental caries risk level in a subject is determined. The risk level is composed of two stages or more, or preferably 3 to 6 stages.

This embodiment shows a mode of the risk level determination unit 231 comprising the rank determination unit 231A and two risk level determination units 231B and 231C. Yet, as long as the risk level is determined for each of the risks based on the measurement result of the parameter that reflects the risk that is obtained by the measurement unit 21, any mode may be employed. For example, the risk level may be directly determined from each of the reflectance data without determining the rank.

Further, the risk level determination unit 231 may combine the parameter corresponding to a certain risk with the parameter corresponding to another risk to thereby determine the risk level of said certain risk. For example, the risk level determination unit 231 may combine one or more parameters that reflect the dental caries risk with one or more parameters that reflect the periodontal disease risk and/or the degree of oral cleanliness to thereby determine the dental caries risk level. Furthermore, the risk level determination unit 231 may combine the parameter corresponding to each of the risks with personal data of the subject to thereby determine the risk level of each of the risks.

The comment determination unit 232 is comprised in the controlling unit 23 and selects a comment corresponding to the risk level determined by the risk level determination unit 231C based on a table showing correlation between the risk level in each of the risks and the comment, the table being stored in the memory unit 24 described later.

The measurement apparatus 2 comprises the display unit 22. The display unit 22 is one mode of output in the present invention and is a unit of displaying the measurement value obtained by the measurement unit 21, the rank determined by the rank determination unit 231A, the risk level determined by the risk level determination unit 231C, the comment selected by the comment determination unit 232, or the like. The display unit 22 is not particularly restricted as long as it is able to display information such as characters or graphic images. For example, a liquid crystal display comprising an LED backlight is suitably used. The displaying by the display unit 22 is carried out in any form such as character, graphic, code, color, or a combination thereof. The display unit 22 can, as necessary, individually display information such as the measurement result of each of the parameters, the determined rank, each of the risk levels, and the comment corresponding thereto. The unit may further display such information collectively in any form such as character, graphic, code, color, or a combination thereof so as to help a doctor or the like make a comprehensive diagnosis of the status of oral hygiene in a subject. Although the display unit 22 is employed as one mode of the output in the present invention in this embodiment, the output may also be any output mode as long as it can be recognized by the doctor, dental hygienist, or subject. For example, the output may be carried out by printing or by voice. In addition, it goes without saying that any of the visual displaying in the display unit, output by printing, output by voice, and the like may be arbitrarily combined to carry out the output of the information.

Further, in the measurement apparatus of the present invention, from the reflectance data of each of the parameters obtained by the measurement unit 21, the value of the parameter may be calculated based on standard curve data (not shown in the Figs.) showing correlation between the parameter and reflectance data. That is, for example, based on the standard curve data (not shown in the Figs.) showing correlation between the mutans bacteria count and the reflectance data, the mutans bacteria count in the test sample may be calculated.

Further, in the measurement apparatus of the present invention, as for each of the parameters, based on a table showing correlation between the rank of each of the parameters and the comment, a comment corresponding to the rank of each of the parameters determined by the rank determination unit 231A may be selected, and further, the selected comment may be outputted.

The measurement apparatus 2 comprises the memory unit 24. The memory unit 24 comprises the program memory unit 241 and the measurement data memory unit 242. The program memory unit 241 stores a program that is loaded into RAM in the controlling unit 23 and is executed by CPU in the controlling unit 23. The measurement data memory unit 242 stores data of the measurement value obtained by the above measurement unit 21. It is preferred that the memory unit 24 further store the result determined by the rank determination unit 231A and the risk level determination units 231B and 231C. The memory unit 24 may also store such fundamental information that is stored in a conventional measurement apparatus, including subject information such as the name and contact address of a subject.

As the measurement apparatus of the present invention, for example, a reflectance measurement device for a urine test strip or for blood test strip can be customized to use in accordance with the analytical tool of the present invention and measurement items thereof. As the reflectance measurement device for a urine test strip, for example, PocketChem UA PU-4010 (manufactured by Arkray, Inc.) can be used. In cases where PocketChem UA PU-4010 is used, measurement by dual-wavelength refractometry can be carried out. In the photometrical unit of PocketChem UA PU-4010, two types of light with different wavelengths, that is, light with a measurement wavelength and light with a reference wavelength can be irradiated from multi LED to a color developing portion and the development of color in the analytical tool can be measured based on the reflectance.

The measurement apparatus of the present invention may or may not be a stand-alone apparatus. That is, each unit may be physically independent of each other as long as it is able to transmit and receive data. For example, the measurement data may be transmitted to another apparatus by utilizing a telecommunication line or the like, and the risk level may be determined in such another apparatus. In addition, the determined risk level may be transmitted to another apparatus by utilizing the telecommunication line or the like, and information such as the determined risk level or the comment based on it may be displayed on such another apparatus.

This embodiment describes a mode of obtaining the reflectance data for measuring each of the parameters by utilizing the test piece comprising the absorptive carrier that holds a reagent for measuring each of the parameters, which is one embodiment of the analytical tool of the present invention. Yet the method for measuring each of the parameters is not limited to the case where the test piece comprising the absorptive carrier is used. As described earlier, such a method can be utilized, for example, in the case where a test piece that does not comprise the absorptive carrier is used and in the case where a reaction with a sample is carried out in a vessel such as a tube. That is, even without using the test piece of the present invention, for example, the test sample can be added into a tube for reaction containing a reagent for measuring an arbitrary parameter to develop a color reaction, thereby to obtain the reflectance data. Thus, in the present invention, the step of "measuring the parameter" can be carried out using the analytical tool of the present invention.

Further, the second aspect of the measurement apparatus of the present invention is a measurement apparatus that comprises the following (A) to (C):

(A) a measurement unit for measuring two or more parameters that reflect the dental caries risk for a test sample obtained from the oral cavity;

(B) a risk level determination unit for determining the level of the dental caries risk from the results measured by the measurement unit; and (C) a display unit for displaying the dental caries risk level determined by the risk level determination unit.

Further, the third aspect of the measurement apparatus of the present invention is, for example, a measurement apparatus that comprises the following (A) to (C):

(A) a measurement unit for measuring two or more parameters that reflect the periodontal disease risk for a test sample obtained from the oral cavity;

(B) a risk level determination unit for determining the level of the periodontal disease risk from the results measured by the measurement unit; and (C) a display unit for displaying the periodontal disease risk level determined by the risk level determination unit.

Further, the fourth aspect of the measurement apparatus of the present invention is, for example, a measurement apparatus that comprises the following (A) to (C):

(A) a measurement unit for measuring two or more parameters that reflect the degree of oral cleanliness for a test sample obtained from the oral cavity;

(B) a risk level determination unit for determining the level of the degree of oral cleanliness from the results measured by the measurement unit; and (C) a display unit for displaying the level of the degree of oral cleanliness determined by the risk level determination unit.

The description presented above in regard to the first aspect of the measurement apparatus of the present invention can be applied mutatis mutandis to the second, third, and fourth aspects of the measurement apparatus of the present invention.

(3) Program of the Present Invention

The first aspect of the program of the present invention is a program that allows a computer to execute the following steps (A) and (B):

(A) the step of allowing a level determination unit to determine, for a test sample obtained from the oral cavity, the levels of the dental caries risk, the periodontal disease risk, and the degree of oral cleanliness based on the measurement results of one or more parameters that reflect the dental caries risk, one or more parameters that reflect the periodontal disease risk, and one or more parameters that reflect the degree of oral cleanliness; and (B) the step of allowing a display unit to display the levels determined in the step (A).

The program of the present invention may further allow the computer to execute the following step (C):

(C) the step of allowing the display unit to display comments based on the levels determined in the step (A).

The program of the present invention is able to allow, for example, the measurement apparatus of the present invention to execute the above steps.

Figure 4:
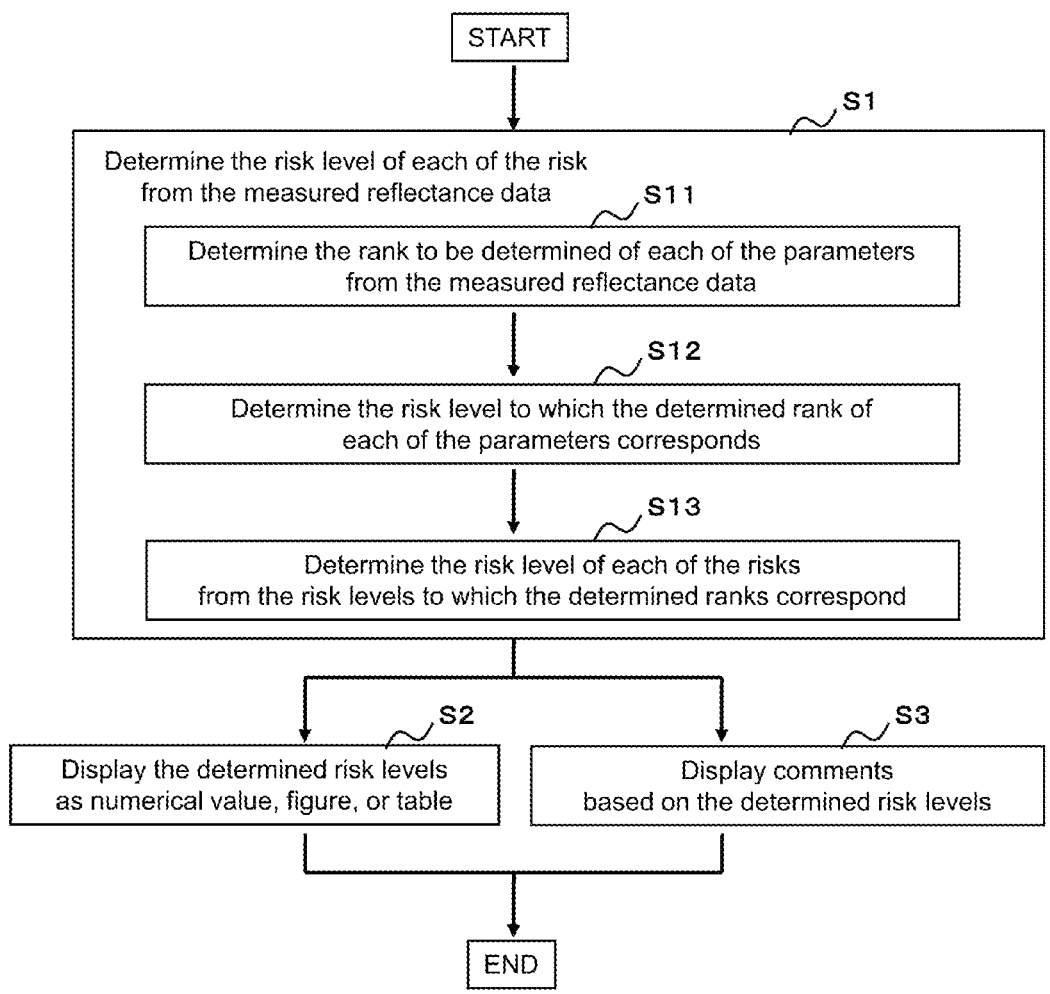
FIG. 4 is a flow chart in one embodiment of the program of the present invention.

In reference to a flow chart in FIG. 4, the program of the present invention will be described below. FIG. 4 shows the steps that the program of the present invention allows the computer to execute in one embodiment of the program of the present invention.

First, the analytical tool of the present invention is placed in the apparatus 2 to measure the reflectance data of each of the absorptive carriers by the measurement unit 21. The reflectance data measured are stored in the measurement data memory unit 242.

In the step S1, each of the risk levels is determined based on the data obtained by the measurement unit 21. The step S1 comprises the steps S11, S12, and S13.

In step S11, the rank determination unit 231A determines the rank of each of the parameters for the test sample based on a table in which correlation between the rank of the parameter that reflects the dental caries risk, the periodontal disease risk, or the degree of oral cleanliness and reflectance data is defined, the table being stored in the memory unit 24. The determined rank is composed of two stages or more, or preferably 3 to 8 stages. To be specific, when the value of the reflectance data for an arbitrary parameter obtained by the measurement unit 21 is x; the rank is divided into n stages (n is an arbitrary integer); the threshold value of the value of the reflectance data at $m^{th}$ stage (m is an arbitrary integer wherein n≥m) for the parameter is $t_m$, m that satisfies $$t_m \geq x > t_{m+1} \qquad (i)$$

is calculated (wherein x=n when $t_n \geq x$), and the rank of the parameter is determined to be the $m^{th}$ stage in n stages.

Once the step S11 is completed, the step S12 follows. In the step 12, the risk level determination unit 231B determines the risk level corresponding to the parameter for the rank of the parameter determined in the step 11 based on a preliminarily defined table.

Once the step S12 is completed the step S13 follows. In the step S13, the risk level determination unit 231C determines, based on the risk level of the parameter determined in the step S12, the risk level of the risk that the parameter reflects. The risk level is composed of two stages or more, or preferably 3 to 6 stages. To be specific, when, for an arbitrary risk, the risk levels determined in the step S12 for the parameters that reflects the risk, the number of which parameters is y, are $p_1, \ldots, p_y$, the risk level z of the risk is calculated by, with $p_{max}$ being the maximum value among $p_1, \ldots, p_y$, $$z = p_{max} + 1 \qquad (ii)$$

(wherein z=n when $p_{max}$=n). In cases where the rank determined for an arbitrary parameter corresponds to plural stages of the risk level, the maximum value among the corresponding risk levels is used as p. For example, when the risk level is composed of 6 stages; the risk level to which the rank of the mutans bacteria count corresponds is 4; the risk level to which the rank of pH corresponds is 2; and the risk level to which the rank of the acid buffering ability corresponds is 3, the risk level of the dental caries risk is calculated as 4+1=5 using the risk level to which the rank of the mutans bacteria count corresponds, which is the maximum among three.

In this embodiment, based on the parameter of which the corresponding risk level is the maximum among one or more parameters that reflect an arbitrary risk, the risk level of the risk is determined. Yet a method for determining the risk level is not particularly restricted as long as the risk level is determined based on the parameter that reflects an arbitrary risk. For example, a mean of the risk levels that correspond to the ranks of one or more parameters may be calculated to determine the risk level based on it. Further, in cases where the level of an arbitrary risk is determined based on the measurement results of plural parameters, such measurement results of plural parameters may be evenly dealt with or may be dealt with in a weighted manner. The weighting can be set, for example, based on the degree of importance of the parameter for an arbitrary risk. For example, in cases where the level of the dental caries risk is determined based on mutans bacteria count, pH, and acid buffering ability, the level of the dental caries risk may be determined by reflecting the measurement result of the mutans bacteria count more strongly than the measurement results of other two parameters. Further, in cases where the determination of a certain risk level is carried out by combining the parameter corresponding to the certain risk level with the parameter corresponding to any other risk and/or the personal data of the subject, the content of the determination step may also be appropriately set.

Once the step S1 is completed, the step S2 follows. In the step S2, the display unit 22 displays the risk levels determined in the step S13 in any form. Examples of the form in which the risk level is displayed include numerical value, graphic, table, and the like. The graphic is not particularly restricted and can be displayed as a graphic in any form such as bar graph or radar chart.

Once the step S1 is completed, the step S3 follows. In the step S3, the comment determination unit 232 selects comments corresponding to the risk levels determined in the step S13 and the display unit 22 displays the selected comments. The comment refers to one showing, for example, what kind of actions should be clinically taken for each of the risks. Examples of the comment include, as for the dental caries risk, "A high level of bacteria causing dental caries is detected, the acid buffering ability of saliva is weak, and hence, the dental caries risk can be said to be high. Make sure to clean your oral cavity after meals. Use of a mouth rinse containing a bactericidal agent is also effective." and, as for the periodontal disease risk, "High levels of occult blood and leukocytes are detected, and hence, the periodontal disease risk can be said to be high. Get rid of plaques with an interdental brush or dental floss to remove the cause of the periodontal disease (gingival inflammation)."

The flow chart shown in FIG. 4 shows a mode in which the step S1 includes the step S11, step S12, and step S3. Yet the step S1 may be any mode as long as the risk level determination unit 231 determines the risk level for each of the risks based on the measurement result of the parameter that reflects the risk obtained by the measurement unit 21. For example, the risk level may be determined from the reflectance data without determining the rank.

Correlation data used in each processing such as correlation between the rank of a parameter and the reflectance data for determining the rank or correlation between the rank and the risk level for determining the risk level from the rank are prepared by, in medical checkup of the oral cavity, dental medical examination, or the like, comparing the measurement value of each of the parameters of the oral test samples obtained from a number of subjects and each of the risk with diagnosis by a dentist to carry out statistical analysis and thereby correlating the value of each of the risk levels with the measurement value of each of the parameters in the test sample. Table 1 shows an example of the values of each of the parameters and the corresponding degrees of risks when the degree of risk is divided into 3 stages for each of the parameters. In Table 1, the value of the acid buffering ability shows the value of final pH when a sample obtained from the oral cavity is dropped to a test strip that holds a certain amount of acid.

TABLE 1

| Degree of risk | Risk low | Risk middle | Risk high | Unit |
| --- | --- | --- | --- | --- |
| Mutans bacteria count | less than 7.0 | not less than 7.0 less than 8.0 | not less than 8.0 | log(CFU/mL) |
| pH | not less than 6.85 | not less than 6.35 less than 6.85 | less than 6.35 | None |

TABLE 1-continued

| Degree of risk | Risk low | Risk middle | Risk high | Unit |
| --- | --- | --- | --- | --- |
| Acid buffering ability | not less than 5.1 | not less than 3.9 less than 5.1 | less than 3.9 | None |
| Calcium | less than 1.0 | not less than 1.0 less than 2.0 | not less than 2.0 | mg/dL |
| Occult blood | less than 0.01 | not less than 0.01 less than 0.2 | not less than 0.2 | mg/dL |
| Leukocyte | less than 4.5 | not less than 4.5 less than 56.0 | not less than 56.0 | U/L |
| Total protein (for Periodontal disease risk determination) | less than 21 | not less than 21 less than 43 | not less than 43 | mg/dL |
| Total protein (for Degree of oral cleanliness determination) | less than 8 | not less than 8 less than 20 | not less than 20 | mg/dL |
| Ammonia | less than 1000 | not less than 1000 less than 3000 | not less than 3000 | µg/dL |

Further, the program of the present invention may also allow the computer to execute the step of displaying each of the parameters that reflect the respective risks as numerical value, figure, or table based on the determined rank. Furthermore, the program of the present invention may also allow the computer to execute the step of displaying a comment based on the determined rank for each of the parameters that reflect the respective risks. The comment about the parameter refers to, for example, one explaining the measurement result of each of the parameters. Examples of the comment about the parameter include "There is a small number of dental caries-causing bacteria in saliva, and that is, you have a good condition.", "The acidity of saliva is around neutral. Keep this condition with daily care.", "Occult blood is found in saliva. The gum might be bleeding, and that is, care is required.", and "The ammonia concentration in saliva is high, and that is, you have a condition where bacteria are actively growing. Active care is required."

This embodiment describes the mode in which the reflectance data are measured by the measurement unit 21 and the measured reflectance data are stored in the measurement data memory unit 242. Yet, instead of the measurement in the measurement unit 21, for example, the result of color reaction in the analytical tool of the present invention may be observed with the naked eye and subsequent processing may be carried out using the result as the reflectance data. That is, the progress of the color reaction in the analytical tool of the present invention can be visually observed under an arbitrary source of light to obtain data for measuring each of the parameters. The arbitrary source of light may be, for example, natural light, fluorescent light, incandescent filament lamp, or the like. It may also be a source of light that is limited to have a specific wavelength. Thus, the step of "measuring the parameter" in the present invention can also be carried out without using the detection apparatus.

The program of the present invention may allow a single computer to execute the respective steps or may allow plural computers that are physically independent to execute the respective steps. For example, the measurement data may be transmitted to another apparatus by utilizing a telecommunication line or the like, and the risk level may be determined in such another apparatus. In addition, the determined risk level may be transmitted to another apparatus by utilizing the telecommunication line or the like, and information such as the determined risk level or the comment based on it may be displayed on such another apparatus. Examples of such a mode include a mode in which the measurement data is inputted on the WEB; the measurement data is transmitted to a server for determination of the risk level; the step of determining the risk level is executed on the server for the determination; and then the determination result is displayed on the WEB. In addition, a charging system based on transmission and receipt of the data by utilizing the telecommunication line or the like may be employed. Examples of such a charging system include a system in which a user is charged at the time of displaying the determination result of the risk level on a WEB browser or at the time of completing download of a file containing the determination result of the risk level. The charging can be carried out in any manner such as charging based on the display or download, or fixed charge by a given period of time such as days, weeks, or months, or the like.

Further, the program of the present invention may be stored in a computer-readable recording medium and provided. The computer-readable recording medium refers to a recording medium in which information such as data or programs is accumulated by electric, magnetic, optical, mechanical, or chemical actions or the like, and the accumulated information can further be read out by the computer. Examples of such a recording medium include floppy (registered trademark) disk, magnetic optical disk, CD-ROM, CD-R/W, DVD-ROM, DVD-R/W, DVD-RAM, DAT, 8 mm tape, memory card, hard disk, ROM (read-only memory), SSD, and the like. Further, the program of the present invention may be recorded as individual programs for every step that is executed by the computer.

Further, the second aspect of the program of the present invention is a program that allows a computer to execute the following step (A) and (B):

(A) the step of allowing a risk level determination unit to determine the level of the dental caries risk based on the measurement results of two or more parameters that reflect the dental caries risk for a test sample obtained from the oral cavity; and (B) the step of allowing a display unit to display the level determined in the step (A).

Further, the third aspect of the program of the present invention is, for example, a program that allows a computer to execute the following step (A) and (B):

(A) the step of allowing a risk level determination unit to determine the level of the periodontal disease risk based on the measurement results of two or more parameters that reflect the periodontal disease risk for a test sample obtained from the oral cavity; and (B) the step of allowing a display unit to display the level determined in the step (A).

Further, the fourth aspect of the program of the present invention is, for example, a program that allows a computer to execute the following step (A) and (B):

(A) the step of allowing a risk level determination unit to determine the level of the degree of oral cleanliness based on the measurement results of two or more parameters that reflect the degree of oral cleanliness for a test sample obtained from the oral cavity; and (B) the step of allowing a display unit to display the level determined in the step (A).

The description presented above in regard to the first aspect of the program of the present invention can be applied mutatis mutandis to the second, third, and fourth aspects of the program of the present invention.

(4) Method of the Present Invention

In the present invention, for example, as shown in the above, the parameters that reflect the condition of the oral cavity in a subject are measured, and the condition of the oral cavity, that is, the risk for oral disease and/or the status of oral hygiene, can be determined based on the measurement results. Accordingly, the present invention provides a method for determining the condition of the oral cavity in a subject.

The first aspect of method of the present invention (hereinafter, referred to also as the first aspect) is a method for determining the condition of the oral cavity in a subject, the method comprising the following (A), (B), and (C):

(A) the step of measuring one or more parameters that reflect the dental caries risk for a test sample obtained from the oral cavity and determining the level of the dental caries risk using the measured parameter(s) as an index(es);

(B) the step of measuring one or more parameters that reflect the periodontal disease risk for the test sample obtained from the oral cavity and determining the level of the periodontal disease risk using the measured parameter(s) as an index(es); and (C) the step of measuring one or more parameters that reflect the degree of oral cleanliness for the test sample obtained from the oral cavity and determining the level of the degree of oral cleanliness using the measured parameter(s) as an index(es).

In method of the present invention, the steps (A) to (C) may simultaneously be carried out or may separately be carried out.

Further, the second aspect of the method of the present invention is a method for determining the dental caries risk in the subject, the method comprising the step of measuring two or more parameters that reflect the dental caries risk for a test sample obtained from the oral cavity and determining the level of the dental caries risk using the measured parameters as indexes.

Further, the third aspect of the method of the present invention is, for example, a method for determining the periodontal disease risk, the method comprising the step of measuring two or more parameters that reflect the dental periodontal disease risk for a test sample obtained from the oral cavity and determining the level of the periodontal disease risk using the measured parameters as indexes.

Further, the fourth aspect of the method of the present invention is, for example, a method for determining the degree of oral cleanliness, the method comprising the step of measuring two or more parameters that reflect the degree of oral cleanliness for a test sample obtained from the oral cavity and determining the level of the degree of oral cleanliness using the measured parameters as indexes.

The method of the present invention can be suitably carried out using, for example, but not limited to, the above-mentioned analytical tool, analytical apparatus, program of the present invention, or the like. Further, the description presented above in regard to the analytical tool, analytical apparatus, program of the present invention, or the like can also be applied mutatis mutandis to the method of the present invention. For example, the method of the present invention may further comprise the step of displaying the determined levels, may comprise the step of displaying comments based on the determined levels, or may comprise the step of displaying the comments based on the measurement results of the parameter.

In the present invention, the test sample obtained from the oral cavity is not particularly limited as long as intended parameters can be measured. For example, saliva at rest, gargle liquid using purified water, or gum saliva collected by stimulating with gum can be used. Of these, the gargle liquid using purified water is preferred. The gargle liquid using purified water is obtained by, for example, holding 3 mL of purified water in the mouth for 10 seconds and spitting it out into a vessel. The volume of the purified water and the period of time of holding the water in the mouth can be appropriately altered as necessary. The obtained test sample can be utilized in subsequent operations without being subjected to particular pretreatment.

The test sample can be brought into reaction directly with each of the reagents for measurement by dropping to the absorptive carrier holding each of the reagents for measurement, which carrier is equipped to the test piece, or by dropping the absorptive carrier for dropping the sample, which carrier is placed in contact with the absorptive carrier holding each of the reagents for measurement. Yet in cases where the quantification of ammonia is carried out using the microdiffusion method, the absorptive carrier that holds the reagent for measurement and the absorptive carrier to which the test sample is dropped are placed without contacting each other and the test sample does not make contact directly with the measurement reagent. Further, in cases where each of the parameters is measured without using the test piece, for example, the test sample can be added into a liquid reaction system containing a reagent for measuring an arbitrary parameter to progress the color reaction.

The following procedure shows an example of a procedure in which the test sample is measured by utilizing the test piece of the present invention, the measurement apparatus of the present invention, and the program of the present invention; and the doctor or the like carries out diagnosis.

1. Collect gargle liquid with 3 mL of purified water as a test sample obtained from the oral cavity.
2. Drop the test sample to each of the absorptive carriers of the test piece of the present invention, or, in cases where the absorptive carrier for dropping the sample is provided, to such a carrier, and measure color changed during a predetermined period of time by the measurement apparatus of the present invention.
3. Determine each of the risk levels based on the measurement result and display it. Further, based on each of the risk levels, display a comment concerning each of the dental caries risk, the periodontal disease risk, and the degree of oral cleanliness.
4. Based on the displayed information, the doctor or the like makes the diagnosis of the risk for oral disease and status of oral hygiene in a subject.

EXAMPLES

By way of examples, the present invention will now be more specifically described below. But the present invention is by no means limited thereto.

Test Example

Investigation of Resazurin Method

As a quantification kit for mutans bacteria using reduction of resazurin as an index, RD test SHOWA™ of Showa Yakuhin Kako Co., Ltd. has been known. Yet the kit requires culturing operation at 37° C. for 15 minutes. In view of this, in this test example, with an aim to measure mutans bacteria at room temperature for 5 minutes, detection conditions for mutans bacteria by the resazurin method were investigated.

A test piece on which an absorptive carrier produced by immersion in a reagent solution for measuring mutans bacteria was placed as an absorptive carrier for measuring mutans bacteria was used as a test group. This reagent solution contains 30 mM sucrose, 0.2% polyvinyl alcohol, 100 mM phosphate buffer solution (pH 6), 0.1 mM methoxy PMS, and 0.12 mM resazurin. A test piece on which an absorptive carrier produced by immersion in a reagent solution having this composition without methoxy PMS being added was used as a control group.

As subjects, those who each were determined to show a high, middle, or low level of mutans bacteria in the oral cavity by DENTOCULT® SM (manufactured by OralCare Inc.), which was a existing mutans bacteria culture determination kit, were recruited. Each of the subjects put 3 mL of purified water in the mouth for 10 seconds and then spitted it out into a vessel to obtain gargle liquid which was used as a test sample.

To the absorptive carrier of each of the test pieces, 10 μL of the test sample obtained from each of the subjects was individually spotted. After the test piece was allowed to stand at 25° C. which was assumed to be room temperature for 5 minutes, the reflectance of the test piece was measured using a reflectance measurement device.

Figure 5:
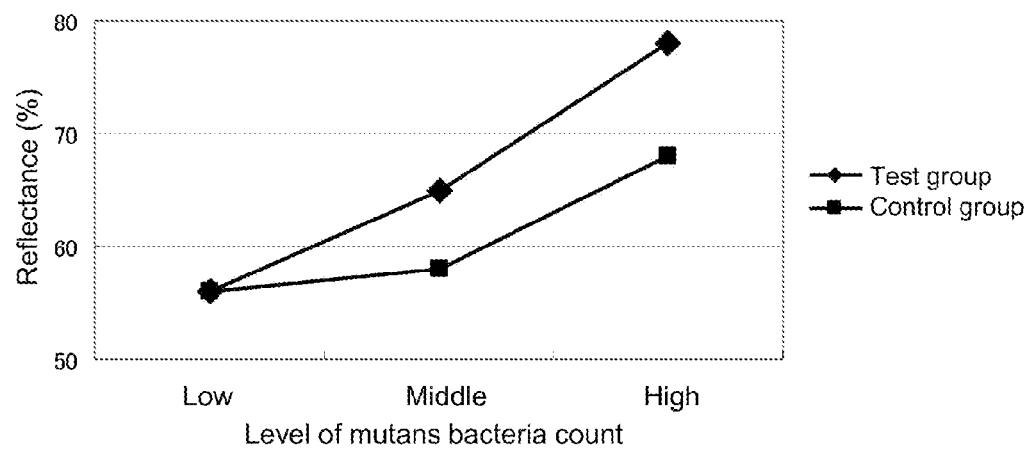
FIG. 5 is a figure showing the correlation between mutans bacteria count and reflectance in the cases of methoxy PMS being added and not being added.

The results are shown in FIG. 5. In the control group without methoxy PMS being added, at the time when 5 minutes had passed at room temperature, the difference in the reflectance between the subject with the low level of the mutans bacteria count and the subject with a medium level of the mutans bacteria count was 2% which was too small to effectively distinguish them from each other. By contrast, in the control group with methoxy PMS being added, differences in the reflectance among 3 degrees were 9 to 13%, and that is, the measurement at room temperature for 5 minutes was feasible. From the above, the addition of methoxy PMS as a reagent for mutans bacteria measurement allows the measurement at room temperature for 5 minutes.

Example 1

Example of Preparation of Test Piece

Preparation of Test Piece

A carrier containing methoxy PMS that was prepared in Test Example 1 was utilized as an absorptive carrier containing a reagent for measurement of mutans bacteria. As carriers for measurement of pH, occult blood, leukocyte count, and total protein concentration, test strips of commercially available AUTION™ Sticks (manufactured by Arkray, Inc.) whose measurement subjects are pH, occult blood, leukocyte count, and total protein concentration were diverted to be used, respectively. As a carrier for acid buffering ability measurement, one obtained by spotting 7 μL of 1 mM tartaric acid to one piece of test strip for pH measurement of AUTION™ Sticks (manufactured by Arkray, Inc.) followed by drying was used. As a carrier for ammonia measurement, a carrier of commercially available AMICHECK™ (manufactured by Arkray, Inc.) was diverted to be used. As a carrier for calcium concentration measurement, a reagent pad of commercially available SPOTCHEM™ II calcium (manufactured by Arkray, Inc.) was diverted to be used. Each of the above carriers was attached to a support carrier made of PET to prepare a test piece comprising reagents for measurement of mutans bacteria count, pH, acid buffering ability, occult blood amount, leukocyte count, ammonia concentration, total protein concentration, and calcium concentration. The carrier for measurement for total protein concentration can be utilized in common for determination of the periodontal disease risk and determination of the degree of oral cleanliness.

Example 2

Prediction of Risk for Oral Disease and Degree of Oral Cleanliness by Saliva Test System (1)

In this Example, whether diagnosis results on the risk for oral disease and the degree of oral cleanliness by a dentist could be predicted base on the measurement results of parameters used in the determination method of the present invention was investigated.

<Method>
(Oral Cavity Index Evaluation)

The following items were used as oral cavity indexes regarding dental caries risk, periodontal disease risk, and degree of oral cleanliness.

Risk of carious state: DMFT
Risk of periodontal disease state: CPI
Degree of oral cleanliness: OHI-DI Each of the oral cavity indexes was diagnosed by a dentist according to a conventional method. DMFT is an index indicating the dental caries experience and is expressed as a total number of, in permanent teeth, the number of untreated carious teeth, the number of teeth lost due to the dental caries, and the number of teeth whose caries has been treated. CPI is an index indicating the degree of treatment needs for the periodontal disease and is calculated based on the criteria of examination results of periodontal tissues using WHO periodontal probes, the results being expressed as scores. With regard to CPI, the upper and lower jaws were divided into six regions of right molar tooth regions, regions of anterior teeth, and left molar tooth regions, and the mean of maximum scores of the respective regions was used for evaluation. OHI-DI is an index indicating the dental plaque cleaning condition and is calculated based on the criteria of the condition of dental plaque deposition onto the tooth surface, the condition being expressed as scores. With regard to OHI-DI, the jaws were divided into six regions in the same manner as CPI and the mean of maximum scores of the respective regiona was used for the evaluation.

(Saliva Test using Test Piece)

Three milliliters of distilled water (Japanese Pharmacopoeia water for injection) was put in the mouth, used for mouth rinsing for 10 seconds, and then spitted out to obtain a test sample. To each of the absorptive carriers placed in the test piece prepared in Example 1, 10 µL of the test sample was individually spotted, and then saliva components were measured. The measurement was carried out using PocketChem UA PU-4010 (manufactured by Arkray, Inc.) as a detection apparatus under conditions of Table 2 at room temperature. Measurement of the mutans bacteria count was carried out by measuring the reflectance 1 minute and 5 minutes after spotting the test sample and calculating reflectance change during the 4 minutes. As for the measurement of items other than the mutans bacteria count, the measurement was carried out by measuring the reflectance when the measurement time period described in Table 2 has passed after the spotting of the test sample. The measurement of the ammonia concentration was carried out by detaching a sample layer and a spacer from a reagent layer 10 seconds after the spotting of the test sample and measuring the reflectance of the reagent layer 60 seconds after the spotting.

TABLE 2

Measurement conditions of the respective parameters

| Name of measurement item | Reaction principle | Measurement time (second) | Photometry wavelength (nm) | Reference wavelength (nm) |
| --- | --- | --- | --- | --- |
| (1) Mutans bacteria count | Resazurin method | 5 minutes | 635 | 760 |
| (2) pH | pH indicator method | 60 | 635 | 760 |
| (3) Occult blood amount | pH indicator method | 60 | 635 | 760 |
| (4) Occult blood amount | Hemoglobin contact activation method | 60 | 635 | — |
| (5) Leukocyte count | Leukocyte esterase method | 60 | 565 | 760 |
| (6) Total protein concentration | Protein error method | 60 | 635 | 760 |
| (7) Ammonia concentration | Microdiffusion method | 60 | 635 | — |
| (8) Calcium concentration | OCPC method | 90 | 565 | 760 |

(Statistical Analysis)

The analysis was performed using data from 231 test subjects. For the analysis, a single regression analysis was performed with each of the oral cavity indexes as a response variable and with each of the saliva component measurement values (reflectance data) as an explanatory variable (Table 3). In addition, a multiple regression analysis was performed for the case where plural saliva component measurement values were combined as explanatory variables and the case where personal data of age, gender, and smoking habits are combined as explanatory variables (Tables 4, 5, and 6). Qualitative variables such as gender or smoking habits were used as dummy variables. After performing each of the regression analyses, a multiple correlation coefficient was determined and estimated as prediction accuracy. The analysis was performed using analysis software JMP5.0 (SAS Institute, Japan).

(Results)

As a result of the single regression analysis with each of the saliva component measurement values as the explanatory variable, correlation was seen between any of the measurement values and the corresponding condition of the oral cavity (Table 3), and it was thus clarified that the prediction of each condition of the oral cavity can be feasible from the saliva component measurement value (reflectance data). Thus, by measuring at least one parameter that reflects each of the dental caries risk, the periodontal disease risk, and the degree of oral cleanliness, the dental caries risk, the periodontal disease risk, and the degree of oral cleanliness can be collectively determined in a simple and quick fashion.

It was also clarified that, by combining plural saliva component measurement values corresponding to a certain condition of the oral cavity, the prediction accuracy (multiple correlation coefficient) was improved (Table 4). Further, it was clarified that, by combining the personal data, the prediction accuracy (multiple correlation coefficient) was more improved (Table 5). Furthermore, it was clarified that, by combining the saliva component measurement value corresponding to a certain condition of the oral cavity with the saliva component measurement value corresponding to another condition of the oral cavity, the prediction accuracy (multiple correlation coefficient) was more improved as well (Table 6). Thus, the combining of the saliva component measurement values or the like improves the prediction accuracy, which enables the determination of the dental caries risk, the periodontal disease risk, and the degree of oral cleanliness with high accuracy.

TABLE 3

Prediction accuracy by single saliva component measurement value

| Examination classification | Response variable (Oral cavity index) | Explanatory variable (Saliva component measurement value) | Prediction accuracy (Multiple correlation coefficient) |
|---|---|---|---|
| Dental caries risk | DMFT | pH | 0.06 |
| | | Acid buffering ability | 0.02 |
| | | Mutans bacteria count | 0.21 |
| Periodontal disease risk | CPI | Occult blood | 0.48 |
| | | Leukocyte | 0.35 |
| | | Calcium | 0.12 |
| | | Protein | 0.51 |
| Degree of oral cleanliness | OHI-DI | Protein | 0.18 |
| | | Ammonia | 0.19 |

TABLE 4

Prediction accuracy when related saliva component measurement values are combined

| Examination classification | Response variable (Oral cavity index) | Explanatory variable (Saliva component measurement value) | Prediction accuracy (Multiple correlation coefficient) |
|---|---|---|---|
| Dental caries risk | DMFT | pH; Acid buffering ability; Mutans bacteria count | 0.24 |
| Periodontal disease risk | CPI | Occult blood; Leukocyte; Protein | 0.55 |
| Degree of oral cleanliness | OHI-DI | Protein; Ammonia | 0.21 |

TABLE 5

Prediction accuracy when related saliva component measurement values are combined with personal data

| Examination classification | Response variable (Oral cavity index) | Explanatory variable | Prediction accuracy (Multiple correlation coefficient) |
|---|---|---|---|
| Dental caries risk | DMFT | pH; Acid buffering ability; Mutans bacteria count; Age, Gender, Smoking habits | 0.52 |
| Periodontal disease risk | CPI | Occult blood; Leukocyte; Protein; Age, Gender, Smoking habits | 0.61 |
| Degree of oral cleanliness | OHI-DI | Protein; Ammonia; Age, Gender, Smoking habits | 0.34 |

TABLE 6

Prediction accuracy when the measurement values of measured seven saliva components are combined with personal data

| Examination classification | Response variable (Oral cavity index) | Explanatory variable | Prediction accuracy (Multiple correlation coefficient) |
|---|---|---|---|
| Dental caries risk | DMFT | Measured seven saliva components; Age, Gender, Smoking habits | 0.54 |
| Periodontal disease risk | CPI | Measured seven saliva components; Age, Gender, Smoking habits | 0.63 |
| Degree of oral cleanliness | OHI-DI | Measured seven saliva components; Age, Gender, Smoking habits | 0.36 |

*In the Table, "measured seven saliva components" refer to the saliva component measurement values other than calcium.

Example 3

Prediction of Risk for Oral Disease and Degree of Oral Cleanliness by Saliva Test System (2)

In this example, whether the number of bacteria, which is a risk for oral disease, could be predicted based on the measurement results of parameters used in the determination method of the present invention was investigated.

<Method>

(Oral Cavity Index Evaluation)

The following items were used as oral cavity indexes concerning the dental caries, the periodontal disease, and the degree of oral cleanliness.

Dental caries risk: Mutans bacteria count in saliva.

Periodontal disease risk: Periodontal disease bacteria count in saliva.

Degree of oral cleanliness: Total bacteria count in saliva.

In regard to the periodontal disease bacteria count, genomes were extracted from saliva using a DNA extraction kit (Nexttecc™), the bacteria counts for three bacterial strains, i.e. *Porphyromonas gingivalis* (P.g.), *Tannerella forsythensis* (T.f.), and *Treponema denticola* (T.d.), all of which are known as representative bacteria in the periodontal disease, were measured by real time PCR, and the total count was used for the evaluation. For all of the bacterial strains, the real time PCR was carried out with the reaction composition and reaction condition shown in Tables 7 and 8. In addition, the sequences of primers and TaqMan® probes used are shown in Tables 9 and 10.

TABLE 7

PCR reaction composition

| Reaction composition | Volume |
|---|---|
| iQ™ supermix (BIO-RAD) | 12.5 μL |
| Primer Forward (Sigma) | 0.5 μL |
| Primer Reverse (Sigma) | 0.5 μL |
| TaqMan™ Probe (Sigma) | 0.5 μL |
| Sterilized water | 10.0 μL |
| Genome extracted | 1.0 μL |

TABLE 8

PCR reaction condition

| Temperature | Time | Number of cycles |
|---|---|---|
| 95° C. | 3 minutes | 1 cycle |
| 95° C. | 10 seconds | 45 cycles |
| 57° C. | 30 seconds | |
| 72° C. | 60 seconds | |

TABLE 9

Primer sequence

| | | | |
|---|---|---|---|
| P. g. | Primer Forward | ACCTTACCCGGGATTGAAATG | SEQ ID NO: 1 |
| | Primer Reverse | CAACCATGCAGCACCTACATAGAA | SEQ ID NO: 2 |
| T. f. | Primer Forward | AGCGATGGTAGCAATACCTGTC | SEQ ID NO: 3 |
| | Primer Reverse | TTCGCCGGGTTATCCCTC | SEQ ID NO: 4 |
| T. d. | Primer Forward | CCGAATGTGCTCATTTACATAAAGGT | SEQ ID NO: 5 |
| | Primer Reverse | GATACCCATCGTTGCCTTGGT | SEQ ID NO: 6 |

TABLE 10

TaqMan™ Probe sequence

| | | |
|---|---|---|
| P. g. | FAM-ATGACTGATGGTGAAAACCGTCTTCCCTTC-TAMRA | SEQ ID NO: 7 |
| T. f. | FAM-TGAGTAACGCGTATGTAACCTGCCCGC-TAMRA | SEQ ID NO: 8 |
| T. d. | FAM-ATGGGCCCGCGTCCCATTAGC-TAMRA | SEQ ID NO: 9 |

In regard to the mutans bacteria count, saliva was diluted 100 to 10000 folds, applied to an MSB plate medium, and incubated for 3 days, at 37° C. under anaerobic conditions, followed by measurement of the number of colonies. In regard to the total bacteria count, saliva was diluted 10000 to 100000 folds, applied to a blood plate medium, and incubated for one week, at 37° C. under anaerobic conditions, followed by measurement of the number of colonies. The composition of each medium is shown in Tables 11 and 12.

TABLE 11

Composition of MSB plate medium

| Reaction composition | Final concentration |
|---|---|
| Mitis Salivarius Agar (Difco) | 90 g/L |
| Bacitracin (Sigma) | 0.2 U/mL |
| Sucrose (Wako) | 50 g/L |

TABLE 12

Composition of blood plate medium

| Reaction composition | Final concentration |
|---|---|
| Todd Hewitt broth (Difco) | 30 g/L |
| Hemin (Wako) | 5 μg/mL |
| Menadione (Wako) | 1 μg/mL |
| Agar (Wako) | 15 g/L |
| Horse defibrinated blood (Nippon Bio-Supp. Center) | 50 g/L |

(Saliva Test using Test Piece of Present Invention)

Three milliliters of distilled water (Japanese Pharmacopoeia water for injection) was put in the mouth, used for mouth rinsing for 10 seconds, and then spitted out to obtain a test sample. To each of the absorptive carriers placed in the test piece, 10 μL of the test sample was individually spotted, and then saliva components were measured. The measurement was carried out using PocketChem UA PU-4010 (manufactured by Arkray, Inc.) as a detection apparatus under conditions of Table 2 at room temperature. Measurement of the mutans bacteria count was carried out by measuring the reflectance 1 minute and 5 minutes after spotting the test sample and calculating reflectance change during the 4 minutes. As for the measurement of items other than the mutans bacteria count, the measurement was carried out by measuring the reflectance when the measurement time period described in Table 2 has passed after the spotting of the test sample. The measurement of the ammonia concentration was carried out by detaching a sample layer and a spacer from a reagent layer 10 seconds after the spotting of the test sample and measuring the reflectance of the reagent layer 60 seconds after the spotting.

(Statistical Analysis)

The analysis was performed using data from 231 test subjects. For the analysis, a single regression analysis was performed with each of the oral cavity indexes as a response variable and with each of the saliva component measurement values (reflectance data) as an explanatory variable (Table 13). In addition, a multiple regression analysis was performed for the case where plural saliva component measurement values were combined as explanatory variables and the case where personal data of age, gender, and smoking habits are combined as explanatory variables (Tables 14, 15, and 16). Qualitative variables such as gender or smoking habits were used as dummy variables. After performing each of the regression analyses, a multiple correlation coefficient was determined and estimated as prediction accuracy. The analysis was performed using analysis software JMP5.0 (SAS Institute, Japan).

(Results)

As a result of the single regression analysis with each of the saliva component measurement values as the explanatory variable, correlation was seen between any of the measurement values and the corresponding condition of the oral cavity (Table 13), and it was thus clarified that the prediction of each condition of the oral cavity can be feasible from the saliva component measurement value (reflectance data). Thus, by measuring at least one parameter that reflects each of the dental caries risk, the periodontal disease risk, and the degree of oral cleanliness, the dental caries risk, the periodontal disease risk, and the degree of oral cleanliness can be collectively determined in a simple and quick fashion.

It was also clarified that, by combining plural saliva component measurement values corresponding to a certain condition of the oral cavity, the prediction accuracy (multiple correlation coefficient) was improved (Table 14). Further, it was clarified that, by combining the personal data, the prediction accuracy (multiple correlation coefficient) was more improved (Table 15). Furthermore, it was clarified that, by combining the saliva component measurement value corresponding to a certain condition of the oral cavity with the saliva component measurement value corresponding to another condition of the oral cavity, the prediction accuracy (multiple correlation coefficient) was more improved as well (Table 16). Thus, the combining of the saliva component measurement values or the like improves the prediction accuracy, which enables the determination of the dental caries risk, the periodontal disease risk, and the degree of oral cleanliness with high accuracy.

TABLE 13

Prediction accuracy by single saliva component measurement value

| Examination classification | Response variable (Oral cavity index) | Explanatory variable (Saliva component measurement value) | Prediction accuracy (Multiple correlation coefficient) |
| --- | --- | --- | --- |
| Dental caries risk | Mutans bacteria count | pH | 0.50 |
|  |  | Acid buffering ability | 0.39 |
|  |  | Mutans bacteria count | 0.59 |
| Periodontal disease risk | periodontal disease bacteria count | Occult blood | 0.60 |
|  |  | Leukocyte | 0.45 |
|  |  | Calcium | 0.13 |
|  |  | Protein | 0.51 |
| Degree of oral cleanliness | Total bacteria count | Protein | 0.49 |
|  |  | Ammonia | 0.61 |

TABLE 14

Predictive accuracy when related saliva component measurement values are combined

| Examination classification | Response variable (Oral cavity index) | Explanatory variable (Saliva component measurement value) | Prediction accuracy (Multiple correlation coefficient) |
| --- | --- | --- | --- |
| Dental caries risk | Mutans bacteria count | pH; Acid buffering; ability; Mutans bacteria count | 0.65 |
| Periodontal disease risk | periodontal disease bacteria count | Occult blood; Leukocyte; Protein | 0.63 |
| Degree of oral cleanliness | Total bacteria count | Protein; Ammonia | 0.64 |

TABLE 15

Predictive precision when related saliva component measurement values are combined with personal data

| Examination classification | Response variable (Oral cavity index) | Explanatory variable | Prediction accuracy (Multiple correlation coefficient) |
| --- | --- | --- | --- |
| Dental caries risk | Mutans bacteria count | pH; Acid buffering ability; Mutans bacteria count; Age, Gender, Smoking habits | 0.66 |
| Periodontal disease risk | periodontal disease bacteria count | Occult blood; Leukocyte; Protein; Age, Gender, Smoking habits | 0.65 |
| Degree of oral cleanliness | Total bacteria count | Protein; Ammonia; Age, Gender, Smoking habits | 0.66 |

TABLE 16

Predictive precision when the measurement values of measured seven saliva components are combined with personal data

| Examination classification | Response variable (Oral cavity index) | Explanatory variable | Prediction accuracy (Multiple correlation coefficient) |
| --- | --- | --- | --- |
| Dental caries risk | Mutans bacteria count | Measured seven saliva components; Age, Gender, Smoking habits | 0.76 |
| Periodontal disease risk | periodontal disease bacteria count | Measured seven saliva components; Age, Gender, Smoking habits | 0.66 |
| Degree of oral cleanliness | Total bacteria count | Measured seven saliva components; Age, Gender, Smoking habits | 0.80 |

*In the Table, "measured seven saliva components" refer to the saliva component measurement values other than calcium.

INDUSTRIAL APPLICABILITY

By the present invention, the parameters that reflect the condition of the oral cavity, that is, the risk for oral disease and/or the status of oral hygiene, can be measured, and the condition of the oral cavity in the subject can be determined based on the measurement results. In particular, by using the analytical tool of the present invention, plural components or properties that reflect the risk for oral disease and the status of oral hygiene can be measured in a short period of time in a single examination, thereby to determine each of the risk levels. The doctor or the like is able to make an objective and comprehensive diagnosis of the risk for oral disease and the status of oral hygiene in the subject based on the determined risk levels. Therefore, the present invention is useful in making the diagnosis of the status of oral hygiene and even giving subsequent care instructions in the single visit.

EXPLANATION OF SYMBOLS

1 - - - Test piece
10 - - - Support carrier
11 - - - Measurement unit of the dental caries risk
11A, 11B, 11C - - - Absorptive carrier holding the reagent for measuring the parameter that reflects the dental caries risk
12 - - - Measurement unit of the periodontal disease risk
12A, 12B, 12C - - - Absorptive carrier holding the reagent for measuring the parameter that reflects the periodontal disease risk
13 - - - Measurement unit of the degree of oral cleanliness
13A, 13B - - - Absorptive carrier holding the reagent for measuring the parameter that reflects the degree of oral cleanliness
14A, 15A - - - Absorptive carrier holding the reagent for measuring an arbitrary parameter
14B, 15B - - - Absorptive carrier to which the test sample is dropped
15C - - - Spacer
2 - - - Measurement apparatus
21 - - - Measurement unit
22 - - - Display unit
23 - - - Controlling unit
231 - - - Risk level determination unit
231A - - - Rank determination unit
231B - - - Risk level determination unit
231C - - - Risk level determination unit
232 - - - Comment determination unit
24 - - - Memory unit
241 - - - Program memory unit
242 - - - Data memory unit

The invention claimed is:

1. A method of determining a condition of an oral cavity in a subject, the method comprising the following (A), (B) and (C):

(A) determining a risk level of dental carries by measuring parameters comprising mutans bacteria count, pH and acid buffering ability from a test sample obtained from the oral cavity;

(B) determining a risk level of periodontal disease by measuring parameters comprising total protein concentration, occult blood amount and leukocyte count from the test sample;

(C) determining a degree of oral cleanliness by measuring parameters comprising ammonia concentration and total protein concentration from the test sample, wherein (A), (B), and (C) are performed using a test piece as an analytical tool, the test piece comprising the following (a), (b), (c), (d), (e), (f) and (g):

(a) an absorptive carrier that contains a reagent for measuring mutans bacteria count;

(b) an absorptive carrier that contains a reagent for measuring pH;

(c) an absorptive carrier that contains a reagent for measuring acid buffering ability;

(d) an absorptive carrier that contains a reagent for measuring total protein concentration;

(e) an absorptive carrier that contains a reagent for measuring occult blood amount;

(f) an absorptive carrier that contains a reagent for measuring leukocyte count; and (g) an absorptive carrier that contains a reagent for measuring ammonia concentration, wherein each of (a), (b), (c), (d), (e), (f) and (g) is supported by a single support carrier, and wherein the plural determinations (A), (B) and (C) result in a comprehensive diagnosis of the condition of the oral cavity during a single examination of the subject.

2. The method according to claim 1 further comprising displaying one or more of the determined levels.

3. The method according to claim 1 further comprising displaying a comment based on one or more of the determined levels.

4. The method according to claim 1,
wherein each of the parameters is measured by a color reaction,
wherein the reagent for measuring mutans bacteria count comprises resazurin, where reaction time for the mutans bacteria count measurement is 1 to 10 minutes,
wherein the reagent for measuring pH comprises a pH indicator, where reaction time for the pH measurement is 30 seconds to 5 minutes,
wherein the reagent for measuring acid buffering ability comprises an acid buffer and a pH indicator, where reaction time for the acid buffering ability measurement is 30 seconds to 5 minutes,
wherein the reagent for measuring total protein concentration comprises a pH indicator, where reaction time for the total protein concentration measurement is 30 seconds to 5 minutes,
wherein the reagent for measuring occult blood amount comprises a peroxide and an indicator that changes color upon oxidation, where reaction time for the occult blood amount measurement is 30 seconds to 5 minutes,
wherein the reagent for measuring leukocyte count comprises a diazonium salt, where reaction time for the leukocyte count measurement is 30 seconds to 5 minutes, and
wherein the reagent for measuring ammonia concentration comprises boric acid buffering agent and a pH indicator, where reaction time for the ammonia concentration measurement is 10 seconds to 5 minutes.

5. The method according to claim 1, wherein the reagent for measuring mutans bacteria count comprises resazurin.

6. The method according to claim 5, wherein the reagent for measuring mutans bacteria count further comprises 1-methoxy-5-methylphenazinium methosulfate.

7. The method according to claim 1, wherein the reagent for measuring pH comprises a pH indicator.

8. The method according to claim 7, wherein the pH indicator comprises bromocresol green and bromoxylenol blue.

9. The method according to claim 1, wherein the reagent for measuring occult blood comprises a peroxide and an indicator that chances color upon oxidation.

10. The method according to claim 1, wherein the reagent for measuring leukocyte count comprises a diazonium salt.

11. The method according to claim 1, wherein the reagent for measuring total protein concentration comprises a pH indicator.

12. The method according to claim 11, wherein the pH indicator comprises tetrabromophenol blue (TBPB), tetrabromophenolphthalein, or 5',5"-dinitro-3',3"-diiodo-3,4,5,6-tetrabromophenol sulfophthalein (DIDNTB).

13. The method according to claim 1, wherein the reagent for measuring ammonia concentration comprises a boric acid buffering agent and a pH indicator.

14. The method according to claim 13, wherein the pH indicator comprises bromcresol green, bromcresol purple or chlorophenol red.

* * * * *

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
accttacccg ggattgaaat g                                      21

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
caaccatgca gcacctacat agaa                                   24

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
agcgatggta gcaatacctg tc                                     22

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
ttcgccgggt tatccctc                                          18
```

```
<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
ccgaatgtgc tcatttacat aaaggt                                          26

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gatacccatc gttgccttgg t                                               21

<210> SEQ ID NO 7
<211> LENGTH: 30
<212> TYPE: DNA
<213> ORGANISM: Artificial Sequence
<220> FEATURE:
<223> OTHER INFORMATION: TaqMan Probe

<400> SEQUENCE: 7
atgactgatg gtgaaaaccg tcttcccttc                                      30

<210> SEQ ID NO 8
<211> LENGTH: 27
<212> TYPE: DNA
<213> ORGANISM: Artificial Sequence
<220> FEATURE:
<223> OTHER INFORMATION: TaqMan Probe

<400> SEQUENCE: 8
tgagtaacgc gtatgtaacc tgcccgc                                         27

<210> SEQ ID NO 9
<211> LENGTH: 21
<212> TYPE: DNA
<213> ORGANISM: Artificial Sequence
<220> FEATURE:
<223> OTHER INFORMATION: TaqMan Probe

<400> SEQUENCE: 9
atgggcccgc gtcccattag c                                               21
```